United States Patent
Nagels et al.

(10) Patent No.: US 7,857,962 B2
(45) Date of Patent: Dec. 28, 2010

(54) POTENTIOMETRIC ELECTRODE, GRADIENT POLYMER, USES AND METHOD OF PREPARATION THEREFOR

(75) Inventors: Luc Nagels, Mechelen (BE); Hugo Bohets, Wilrijk (BE); Mohamedilias Jimidar, Turnhout (BE)

(73) Assignee: Universiteit Antwerpen, Antwerp (BE)

( * ) Notice: Subject to any disclaimer, the term of this patent is extended or adjusted under 35 U.S.C. 154(b) by 1086 days.

(21) Appl. No.: 11/587,711

(22) PCT Filed: Apr. 27, 2005

(86) PCT No.: PCT/EP2005/004501

§ 371 (c)(1),
(2), (4) Date: Oct. 26, 2006

(87) PCT Pub. No.: WO2005/103664

PCT Pub. Date: Nov. 3, 2005

(65) Prior Publication Data

US 2008/0000290 A1    Jan. 3, 2008

(30) Foreign Application Priority Data

Apr. 27, 2004    (WO) .............. PCT/EP/2004/004431

(51) Int. Cl.
   *G01N 27/26* (2006.01)
(52) U.S. Cl. .................. 205/489; 204/417
(58) Field of Classification Search .............. 205/789, 205/789.5; 204/416, 417, 418; 429/231.8
   See application file for complete search history.

(56) References Cited

U.S. PATENT DOCUMENTS 4,454,007 A    6/1984    Pace

| 5,177,221 A | 1/1993 | Cram et al. |
| 5,288,388 A | 2/1994 | Fombon |
| 5,344,547 A | 9/1994 | Vlasov et al. |
| 6,099,965 A * | 8/2000 | Tennent et al. .............. 428/408 |
| 2002/0038762 A1 | 4/2002 | Eventov et al. |

FOREIGN PATENT DOCUMENTS

EP    0 138 150    4/1985

OTHER PUBLICATIONS

Jarzebinska, A., et al., "Nanoscopic complexes of dendrimers based on hexaazamacrocycle—synthesis and characterization", Materials Science and Engineering C, vol. 18, 2001, p. 61-64.*

(Continued)

*Primary Examiner*—Nam X Nguyen
*Assistant Examiner*—J. Christopher Ball
(74) *Attorney, Agent, or Firm*—Knobbe, Martens, Olson & Bear, LLP

(57) ABSTRACT

The present invention relates to a potentiometric electrode and gradient polymer, both comprising electrically conducting particles, which increase in concentration away from one surface, ionophore molecules, which increase in concentration towards the same surface surface, and an electrical connection which passes proximal to said electrically conducting particles. The invention further relates to devices incorporating said electrode or gradient polymer, and to a method for their preparation. The new materials are highly robust and reliable.

33 Claims, 20 Drawing Sheets

OTHER PUBLICATIONS

Pietraszkiewicz, M., and R. Gasiorowski, "Novel Access to Polyazamacrocycles: Non-Template Cyclization of Terephthalaldehyde and Aliphatic Polyamines", Chemische Berichte, vol. 123, No. 3, 1990, p. 405-406.*

Zielinska, et al. "Potentiometric Detection of Organic Acids in Liquid Chromatography Using Polymeric Liquid Membrane Electrodes Incorporating Macrocyclic Hexaamines," *Journal of Chromatography A*, vol. 915, pp. 25-33, 2001.

Vissers, et al. "Characteristics of New Composite- and Classical Potentiometric Sensors for the Determination of Pharmaceutical Drugs," *Electrochimica Acta*, vol. 51, pp. 5062-5069, 2006.

* cited by examiner

Figure 1:
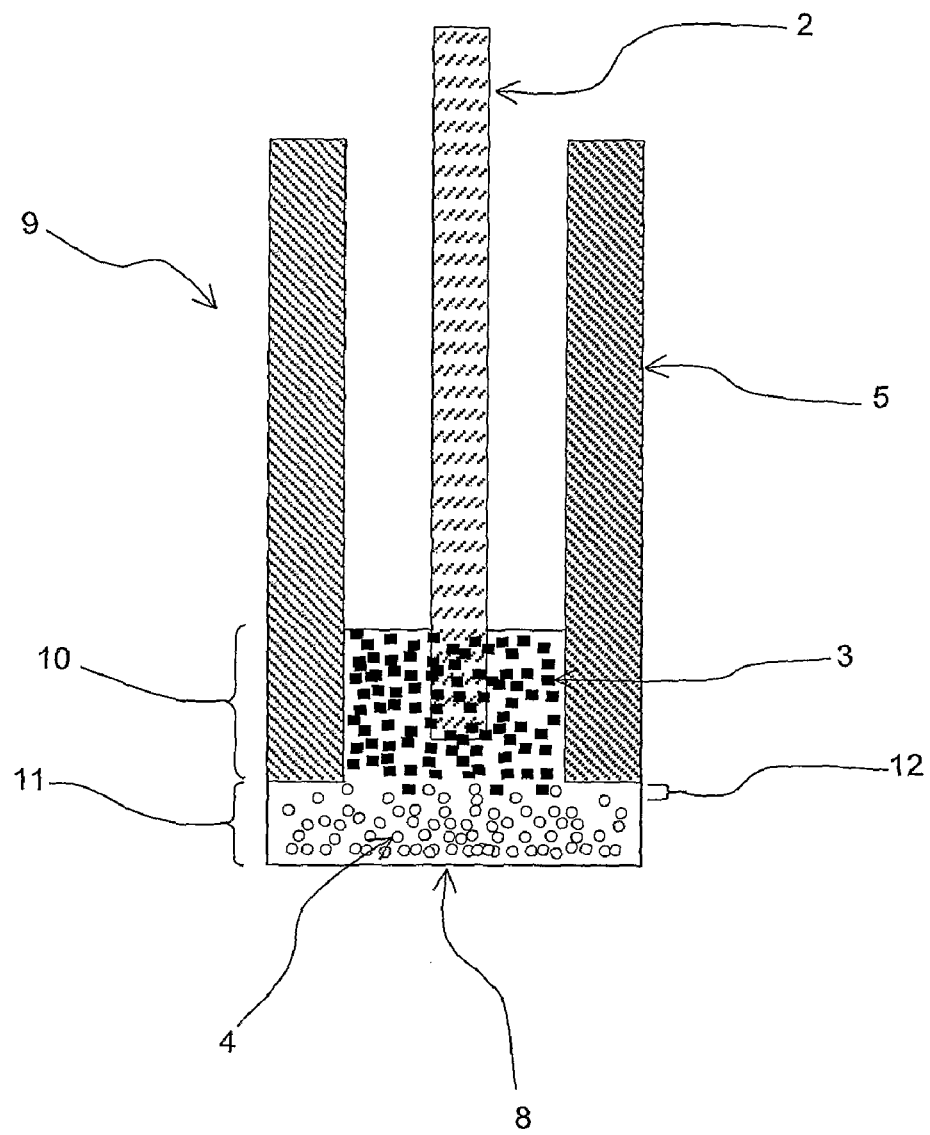
Figures 2, 11:
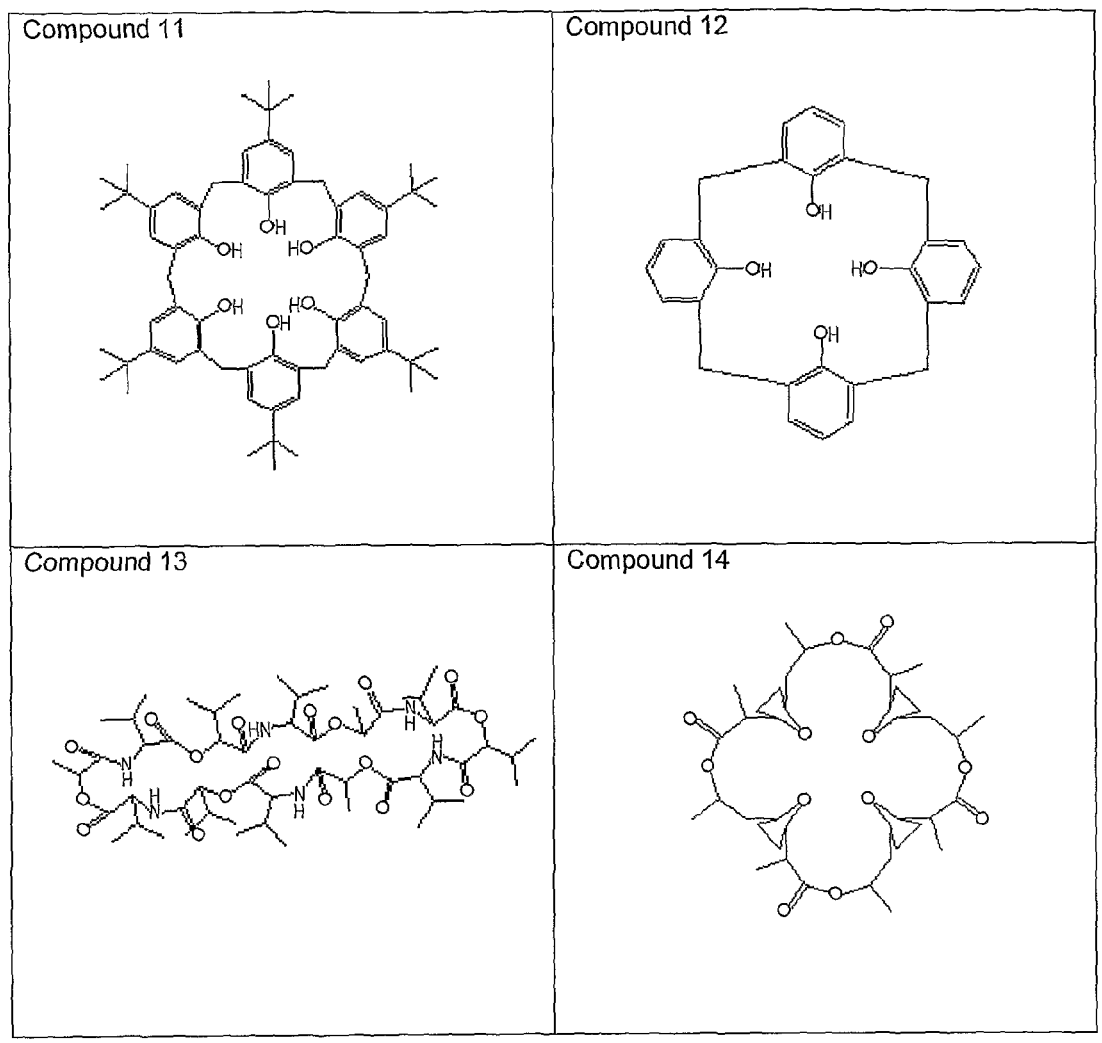
Figures 3, 11:
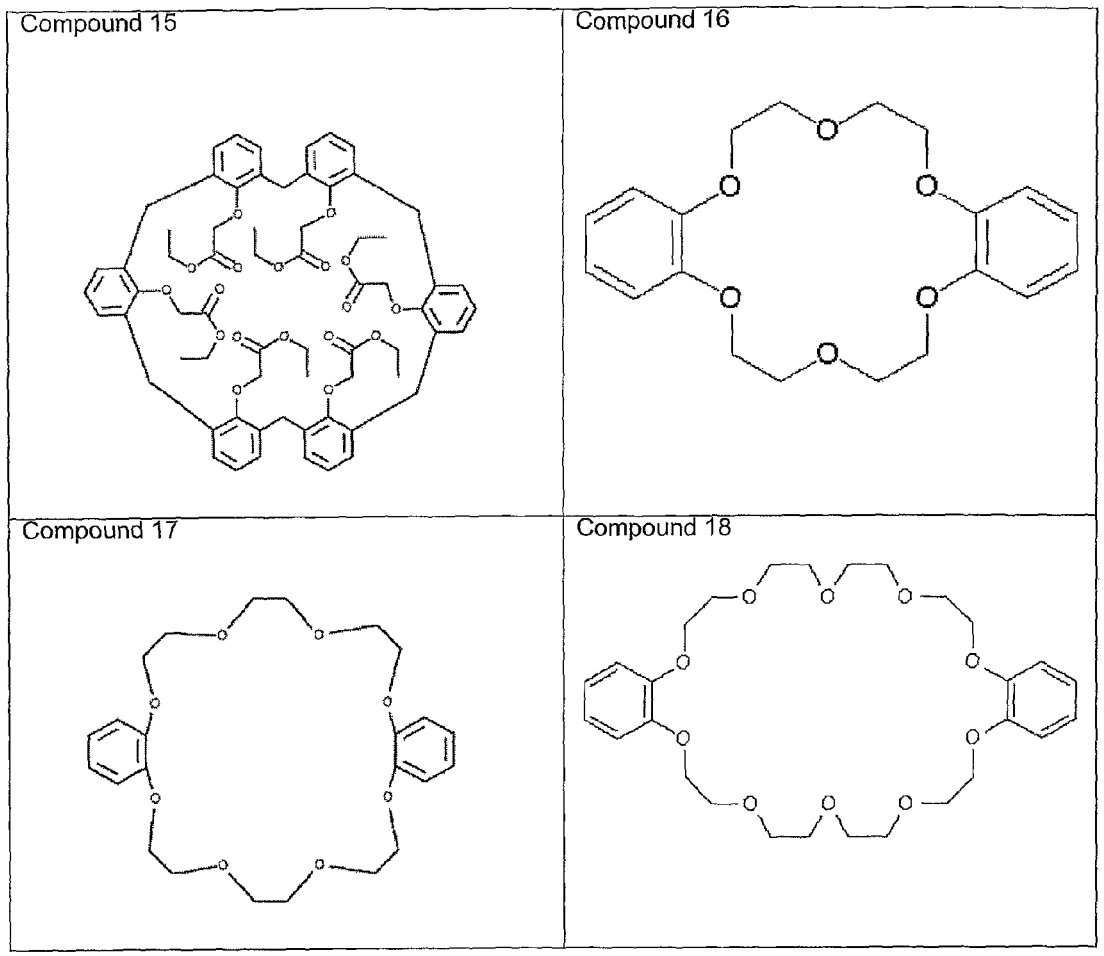
Figures 4, 11:
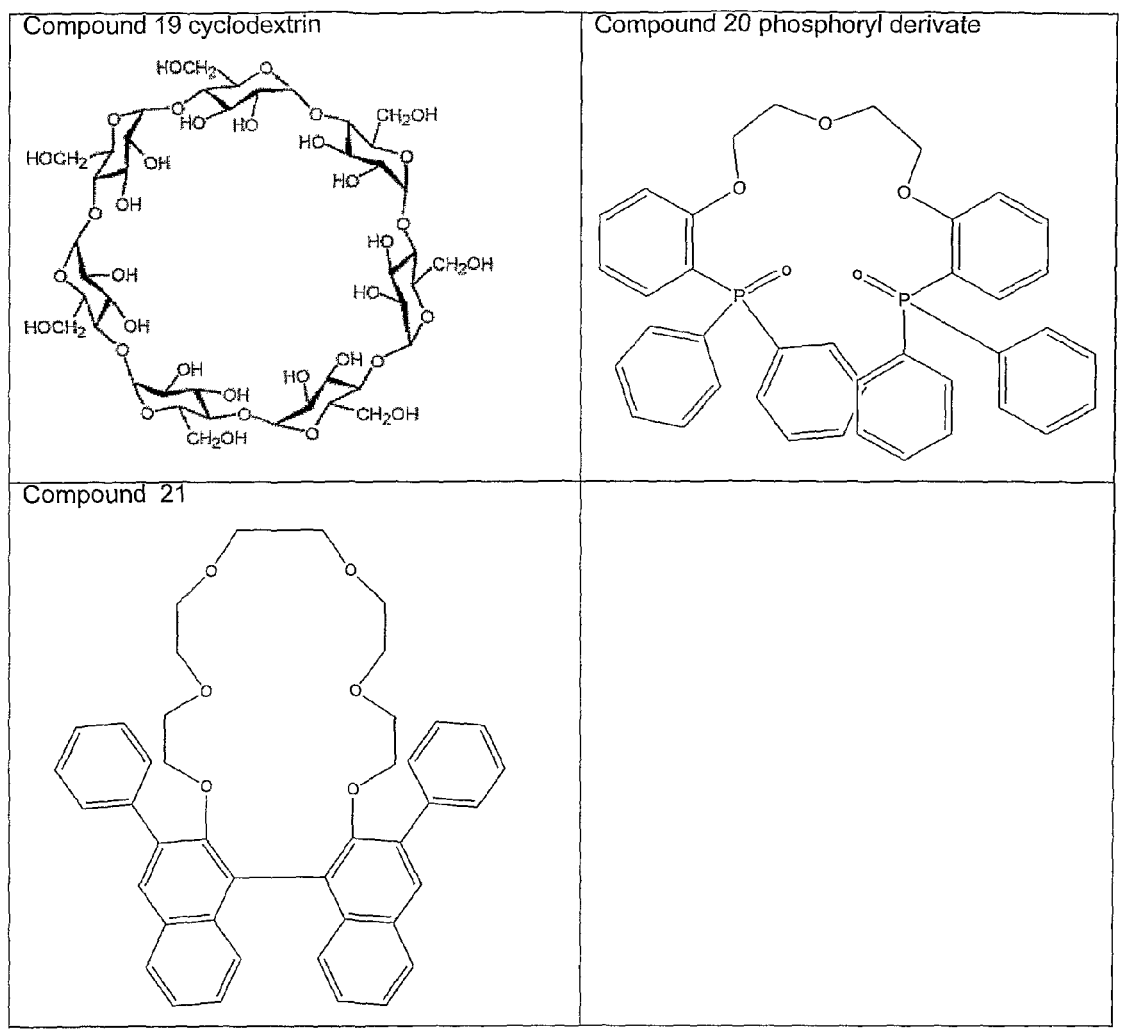

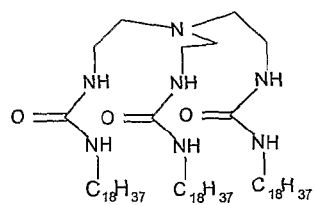
compound 1
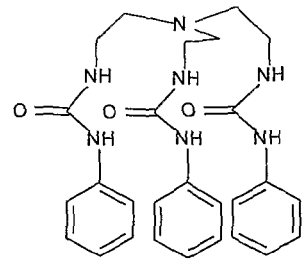
compound 2
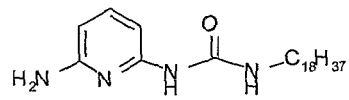
compound 3
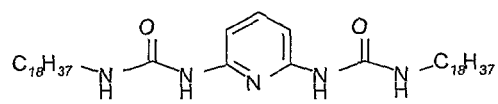
compound 4
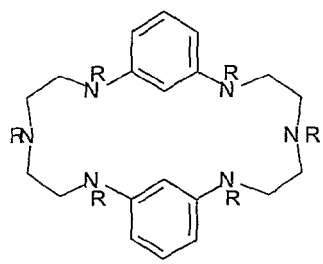
compound 5  R = $C_8H_{17}$
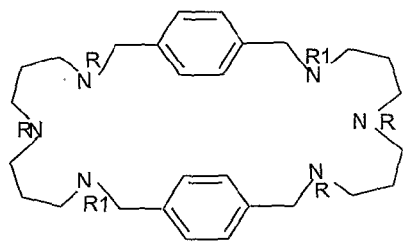
compound 6  R = H, R1 = $C_{10}H_{21}$
compound 8  R = R1 = $(CH_2)_3NHCONHC_{18}H_{37}$
compound 9  R = R1 = $CH_2CONHC_2H_4N(C_2H_4NHCONHC_{18}H_{37})_2$
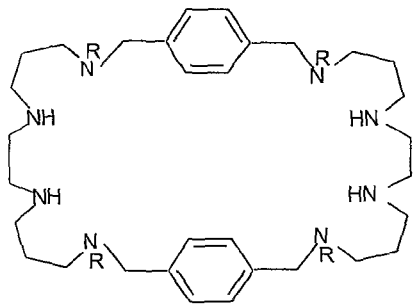
compound 7  R = $C_{10}H_{21}$
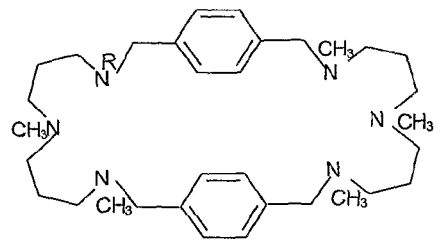
compound 10  R = $(CH_2)_4OCONHC_{18}H_{37}$
FIGURE 11-1

POTENTIOMETRIC ELECTRODE, GRADIENT POLYMER, USES AND METHOD OF PREPARATION THEREFOR

RELATED APPLICATIONS

This application is the U.S. National Phase under 35 U.S.C. §371 of International Application PCT/EP2005/004501, filed Apr. 27, 2005 which claims priority to PCT/EP2004/004431, filed Apr. 27, 2004.

FIELD OF THE INVENTION

The present invention relates to the field of potentiometric electrodes, gradient polymers and electrical or sensing components comprising said gradients. It also relates to methods for preparing potentiometric electrodes and gradient polymers.

BACKGROUND TO THE INVENTION

Potentiometric electrodes have widespread applications in the fields of biology, chemistry, and medicine. They are used for detecting and measuring the concentration of ion species in solution, the best known example being the pH-meter. The operating principles are well known.

Potentiometric electrodes can also be used as sensors to detect analytes. Analyte may be any desired target that has a corresponding ionophore that is capable of specifically interacting with target substances of interest. Examples of analytes include organic acids, amines, amino alcohols and pharmaceutical drugs. Such electrodes combined with suitable ionophores are capable of detecting a corresponding analyte. The applications of potentiometric electrodes are numerous, including biomedical research, clinical testing, obtaining drug data, industrial pollution testing, food testing and chemical-process control.

At present, there is a strong drive towards application of electrochemical sensing of ionizable substances in miniaturized techniques, such as capillary electrophoresis, and microchip arrays.

Potentiometric electrodes coupled to separation methods (e.g. High Performance Liquid Chromatography, "HPLC") are practically non-existing. However, such methods can give access to many interesting substances which are available in minute quantities only, and often in admixture with other substances. For these applications, sensors with low specificity are required, in contrast to batch techniques in which high specificity is required.

Patent application EP 0 767 372 A1 discloses a substrate electrode comprising an epoxy resin (or polyester-, or polyimide resin) cylinder containing carbon fibers. A classical poly (vinylchloride) (PVC)-based potentiometric membrane is coated on this substrate electrode. The authors made a sophisticated design to optimize the membrane—substrate electrode contact, Patent application EP 0 684 466 A2 discloses a substrate electrode which is a solid conductor or semiconductor. It is coated with a classical PVC/plasticiser/ionophore mixture, plus an additional conductive polymer.

Patent application EP 0 300 662 A2 discloses a conventional coated wire potentiometric electrode which is optimized for the measurement of cationic and anionic surfactants.

U.S. Pat. No. 5,552,032 describes a chloride (or generally, a halide ion) sensitive potentiometric electrode. It is a variant of the potentiometric sensors based on silver halide crystal electrode materials.

A problem with potentiometric electrodes of the prior art is the lack of stability (potential drift), mechanical robustness and sensitivity. Their life span is unpredictable, so requiring regular financial expenditure in the form of maintenance on the part of the owner. Furthermore, they are unsuitable for use in HLPC detection and Capillary Electrophoresis (CE) detection, dissolution testing of pharmaceuticals, wherein their behaviour is difficult to predict, and some designs cannot be used with the ion-pairing agent frequently used in HPLC and CE separations or with the detergents used in dissolution testing.

There is clearly a need for a new potentiometric electrode, suitable for use in sensing analytes which overcomes the problems of the prior art.

SUMMARY OF THE INVENTION

One embodiment of the present invention is a potentiometric electrode for selective analyte detection in a sample comprising:
  a sensing body made from polymeric material comprising:
    electrically conducting particles, which increase in concentration away from a sample contact surface,
    ionophore molecules, which increase in concentration towards the sample contact surface, and
    an electrical connection which passes proximal to said electrically conducting particles.

Another embodiment of the present invention is a potentiometric electrode as described above wherein said electrical connection is made of copper.

Another embodiment of the present invention is a potentiometric electrode as described above wherein the polymeric material is polyvinyl chloride.

Another embodiment of the present invention is a potentiometric electrode as described above wherein the polymeric material comprises one or more of poly(n-butylacrylate), poly(butylacrylate), cross-linked poly(butylacrylate), polycarbonate, polystyrene, polymethylmethacrylate, poly(vinylchloride-co-vinylacetate-co-vinylalcohol), polysiloxane, DC 200 silicon oil, polyvinyl chloride, or high molecular weight polyvinyl chloride.

Another embodiment of the present invention is a potentiometric electrode as described above, wherein the maximum concentration of electrically conducting particles is 65% w/w.

Another embodiment of the present invention is a potentiometric electrode as described above, wherein the electrically conducting particles are graphite powder.

Another embodiment of the present invention is a potentiometric electrode as described above wherein said electrically conducting particles are any of carbon powder, graphite powder, synthetic graphite powder with a diameter of 1 to 2 micrometer.

Another embodiment of the present invention is a potentiometric electrode as described above, wherein said electrically conducting particles are any of electropolymerised materials, oxidized polypyrrole and its derivatives, oxidized polythiophenes, polyaniline, noble metals, gold or platinum.

Another embodiment of the present invention is a potentiometric electrode as described above wherein the ionophore molecules are one or more selected from the group consisting of compounds 1 to 10 in FIG. 11.

Another embodiment of the present invention is a potentiometric electrode as described above said ionophore molecules are one or more selected from the group consisting of tetra (p-chloro)phenylborate, methyltridodecylammoniumchloride and compounds 11 to 21 in FIG. 11.

Another embodiment of the present invention is a potentiometric electrode as described above wherein the sensing body is cylindrical in shape.

Another embodiment of the present invention is a potentiometric electrode as described above wherein the polymeric material is at least partly enclosed in a housing.

Another embodiment of the present invention is a potentiometric electrode as described above wherein the ionophore molecules and the electrically conducting particles mix only in a transition region.

Another embodiment of the present invention is a potentiometric electrode as described above wherein the region of polymeric material comprising ionophore molecules, comprises more plasticiser than the remainder of the polymeric material.

Another embodiment of the present invention is a chromatographic flow cell comprising an potentiometric electrode as described above.

Another embodiment of the present invention is a chromatographic flow cell as described above, comprising a nozzle allowing eluent to be sprayed onto a sample contact surface.

Another embodiment of the present invention is a method for making a potentiometric electrode as described above comprising the steps of:

(a) preparing a suspension of electrically conducting particles and in a solution of polymeric material in a solvent, (b) inserting an electrical conductor therein, (c) drying the suspension, so forming a solid composite polymer with electrically conducting particles therein, (d) adding, to a surface of the composite of step (c) a solution of polymeric material, electrically conducting particles and ionophore molecules, (e) drying the mixture, (f) repeating steps (d) and (e), with decreasing concentrations of electrically conducting particles, and increasing concentrations of ionophore molecules, and (g) obtaining a potentiometric electrode.

Another embodiment of the present invention is a method for making a potentiometric electrode as described above comprising the steps of:

(a) preparing a suspension of electrically conducting particles in a solution of polymer in a solvent, (b) inserting an electrical conductor therein, (c) drying the suspension, so forming a solid composite polymer with electrically conducting particles therein, (d1) adding, to a surface of the particle/polymer composite, a solution of polymer and ionophore.

(e1) drying the mixture.

(f1) repeating steps (d1) and (e1), and (g1) obtaining a potentiometric electrode with composite gradient properties and no interfaces.

Another embodiment of the present invention is a method for making a potentiometric electrode as described above comprising the steps of:

(a1) preparing a suspension of electrically conducting particles in a solution of polymer in a solvent, (b1) injecting the suspension into distilled water, so forming a precipitate, (b2) reducing the size of the precipitate to form a residue, (c1) drying the residue by pressing to form a conducting particle/polymer composite, followed by steps (d) to (g) or (d1) to (g1) as defined above.

Another embodiment of the present invention is a method as described above wherein the relative proportion (w/w) of said electrically conducting particles to said polymer is in the range 20 to 90% electrically conducting particles.

Another embodiment of the present invention is a method as described above wherein said electrically conducting particles are any of carbon powder, graphite powder, synthetic graphite powder with a diameter of 1 to 2 micrometer.

Another embodiment of the present invention is a method as described above wherein said electrically conducting particles are any of electropolymerised materials, oxidized polypyrrole and its derivatives, oxidized polythiophenes, polyaniline, noble metals, gold or platinum.

Another embodiment of the present invention is a method as described above wherein said polymer is any of poly(n-butylacrylate), poly(butylacrylate), polycarbonate, polystyrene, polymethylmethacrylate, poly(vinylchloride-co-vinylacetate-co-vinylalcohol), polysiloxane, DC 200 silicone oil or high molecule weight polyvinyl chloride (PVC).

Another embodiment of the present invention is a method as described above wherein the proportion (w/v) of solid components (electrically conducting particles and polymer), to solvent in the suspension of step (a) or (a1) is 1:(1 to 10).

Another embodiment of the present invention is a method as described above wherein the solvent of step (a) or (a1) is any of DMSO, 111 trichloro ethane, $CCl_4$, N,N-dimethylformamide and N,N-dimethylacetamide, and THF.

Another embodiment of the present invention is a method as described above wherein the solvent of step (d) or (d1) is any of DMSO, 111 trichloro ethane, $CCl_4$, N,N-dimethylformamide and N,N-dimethylacetamide, and THF.

Another embodiment of the present invention is a method as described above wherein said ionophore molecules are one or more selected from the group consisting of compounds 1 to 10 in FIG. 11.

Another embodiment of the present invention is a method as described above wherein said ionophore molecules are one or more selected from the group consisting of tetra(p-chloro) phenylborate, methyltridodecylammoniumchloride and compounds 11 to 21 in FIG. 11

Another embodiment of the present invention is a method as described above wherein said polymer in step (d) or (d1) is any which is in the rubber phase at or below room temperature.

Another embodiment of the present invention is a method as described above wherein said polymer in step (d) or (d1) is poly(butylacrylate).

Another embodiment of the present invention is a method as described above wherein composition of the solid components (polymer and ionophore) in step (d) or (d1) comprises 85 to 99% polymer.

Another embodiment of the present invention is a method as described above wherein the composition of the solid components (polymer and ionophore) in step (d) or (d1), comprises 0.1 to 3% ionophore.

Another embodiment of the present invention is a method as described above wherein the ratio (w/v) of solid components (polymer and ionophore) to solvent is 1:(8 to 12) in step (d) or (d1).

Another embodiment of the present invention is a method as described above wherein the solution of step (d) or (d1) further comprises plasticiser.

Another embodiment of the present invention is a method as described above wherein the composition of the membrane components (plasticiser, polymer and ionophore) in step (d) or (d1) comprises 55 to 75% plasticiser.

Another embodiment of the present invention is a method as described above wherein said plasticiser is any of o-nitrophenyl octyl ether, dioctyl sebacate, bis(2-ethylhexyl)phthalate, tris(2-ethylhexyl)phosphate or tris(2-ethylhexyl)trimellitate.

Another embodiment of the present invention is a method as described above wherein the composition of the membrane components (plasticiser, polymer and ionophore) in step (d) or (d1), comprise 28 to 38% polymer.

Another embodiment of the present invention is a method as described above wherein the composition of the membrane components (plasticiser, polymer and ionophore) in step (d) or (d1), comprises 0.1 to 3% ionophore.

Another embodiment of the present invention is a method as described above wherein the ratio (w/v) of membrane components (plasticiser, polymer and ionophore) to solvent is 1:(8 to 12) in step (d) or (d1).

Another embodiment of the present invention is a method for making a potentiometric electrode as described comprising the steps of a3) preparing a paste comprising:
    a suspension of electrically conducting particles defined in step (a) or step (a1) above, with or without solvent, or
    a suspension of electrically conducting particles defined in step (a) or step (a1) above, with or without solvent, in which the polymer is polysiloxane, or
    a suspension of electrically conducting particles defined in step (a) or step (a1) above, with or without solvent, in which the polymer is DC 200 silicon oil, b3) inserting an electrical conductor therein, c3) adding to a surface of the particle/polymer composite a mixture comprising base, curing agent, and ionophore, optionally dissolved in solvent.

d3) degassing the construction, e3) heating the construction, and f3) obtaining a potentiometric electrode with composite gradient properties and no interfaces.

Another embodiment of the present invention is a method as described above wherein the solvent of step (a) is tetrahydrofuran.

Another embodiment of the present invention is a method as described above wherein the maximum concentration of electrically conducting particles is 20 to 90% w/w.

Another embodiment of the present invention is a method as described above wherein the maximum concentration of ionophore molecules is 0.1 to 5% w/w.

Another embodiment of the present invention is a gradient polymer comprising:
    electrically conducting particles, which increase in concentration away from a surface,
    ionophore molecules, which increase in concentration towards the surface.

Another embodiment of the present invention is a gradient polymer substantially formed from polymeric material comprising two surfaces, said polymeric material comprising:
    electrically conducting particles which decrease in concentration away from one surface,
    ionophore molecules decease in concentration away from the other surface.

Another embodiment of the present invention is a gradient polymer substantially formed from polymeric material comprising two surfaces, said polymeric material comprising electrically conducting particles, which decrease in concentration away from both surfaces.

Another embodiment of the present invention is a gradient polymer as described above, wherein the polymer comprises one or more of the polymers defined above.

Another embodiment of the present invention is a gradient polymer as described above, wherein the polymer comprises one or more of the electrically conducting particles defined above.

Another embodiment of the present invention is a gradient polymer as described above, wherein the polymer comprises one or more of the ionophores defined above.

Another embodiment of the present invention is a gradient polymer as described above, comprising the steps defined in the methods above, wherein one or more additional electrical conductors are incorporated.

Another embodiment of the present invention is a method for preparing a gradient polymer as described above comprising the steps defined in the methods above, wherein the ionophore of step (d) and (d1) is absent.

Another embodiment of the present invention is a method for preparing a gradient polymer comprising the steps defined in the methods above, further comprising the step of joining two gradient polymers together at the surfaces of lowest concentration of electrically conducting particles.

Another embodiment of the present invention is a battery comprising gradient polymer as described above.

Another embodiment of the present invention is a variable resistor gradient polymer as described above.

Another embodiment of the present invention is a variable capacitor gradient polymer as described above.

Another embodiment of the present invention is a pressure sensor gradient polymer as described above.

Another embodiment of the present invention is a solvent or lipophilic molecule sensor gradient polymer as described above.

Another embodiment of the present invention is a use of a gradient polymer as described above for sensing analytes.

Another embodiment of the present invention is a use of a potentiometric electrode as described above for inline monitoring the dissolution of a drug from a drug formulation.

FIGURES

FIG. 1. An example of a potentiometric electrode according to the invention.

Figure 2:
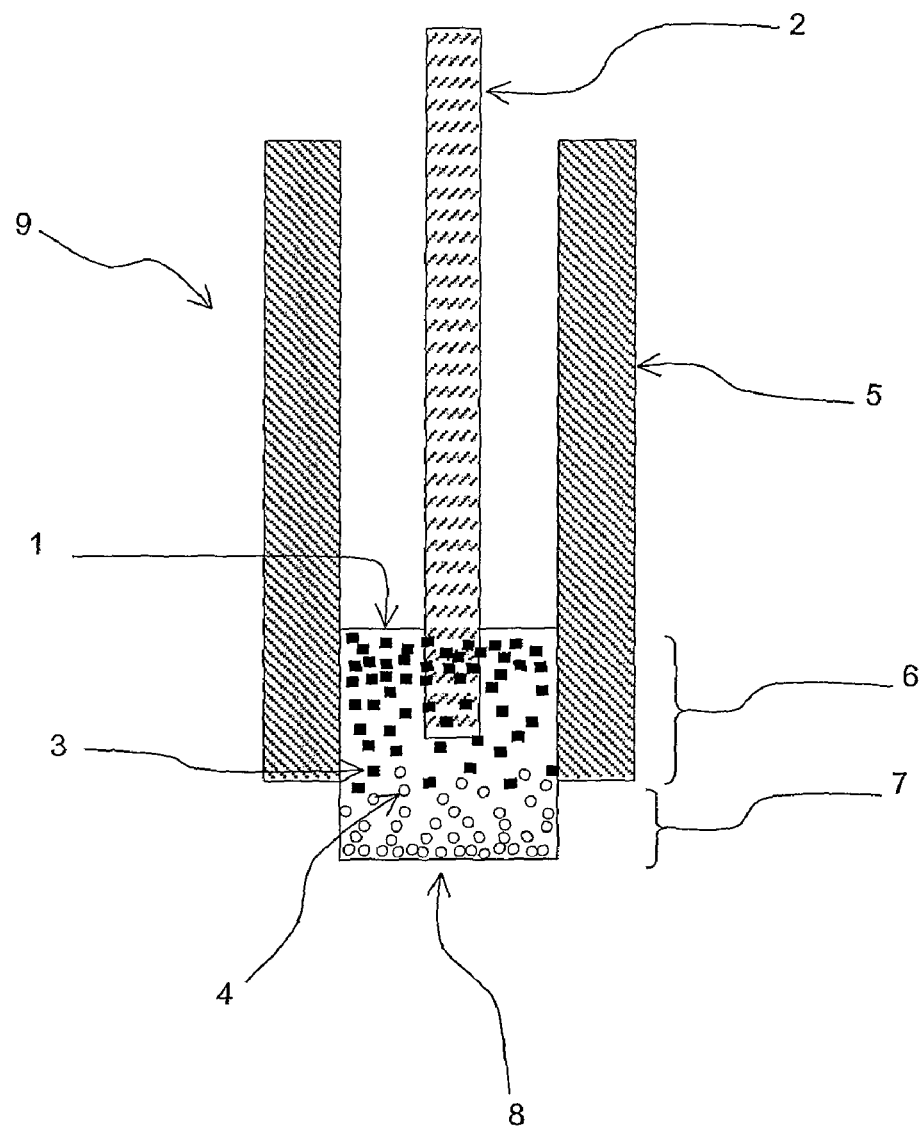

FIG. 2. An example of a potentiometric electrode according to the invention.

Figure 3:
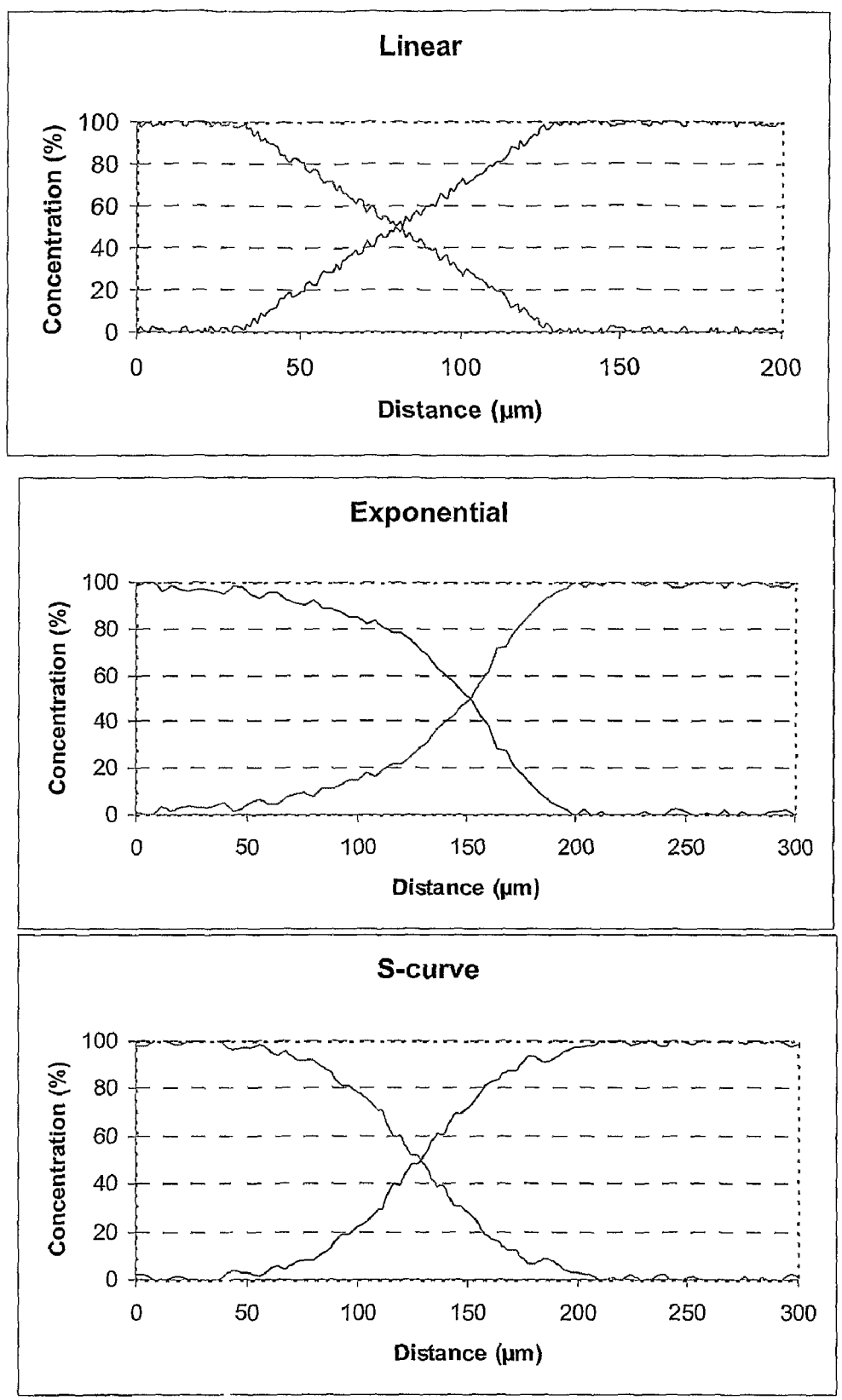

FIG. 3. Examples (a, b and c) of continuous gradient polymers with noise due to uneven distribution and particle size.

Figure 4:
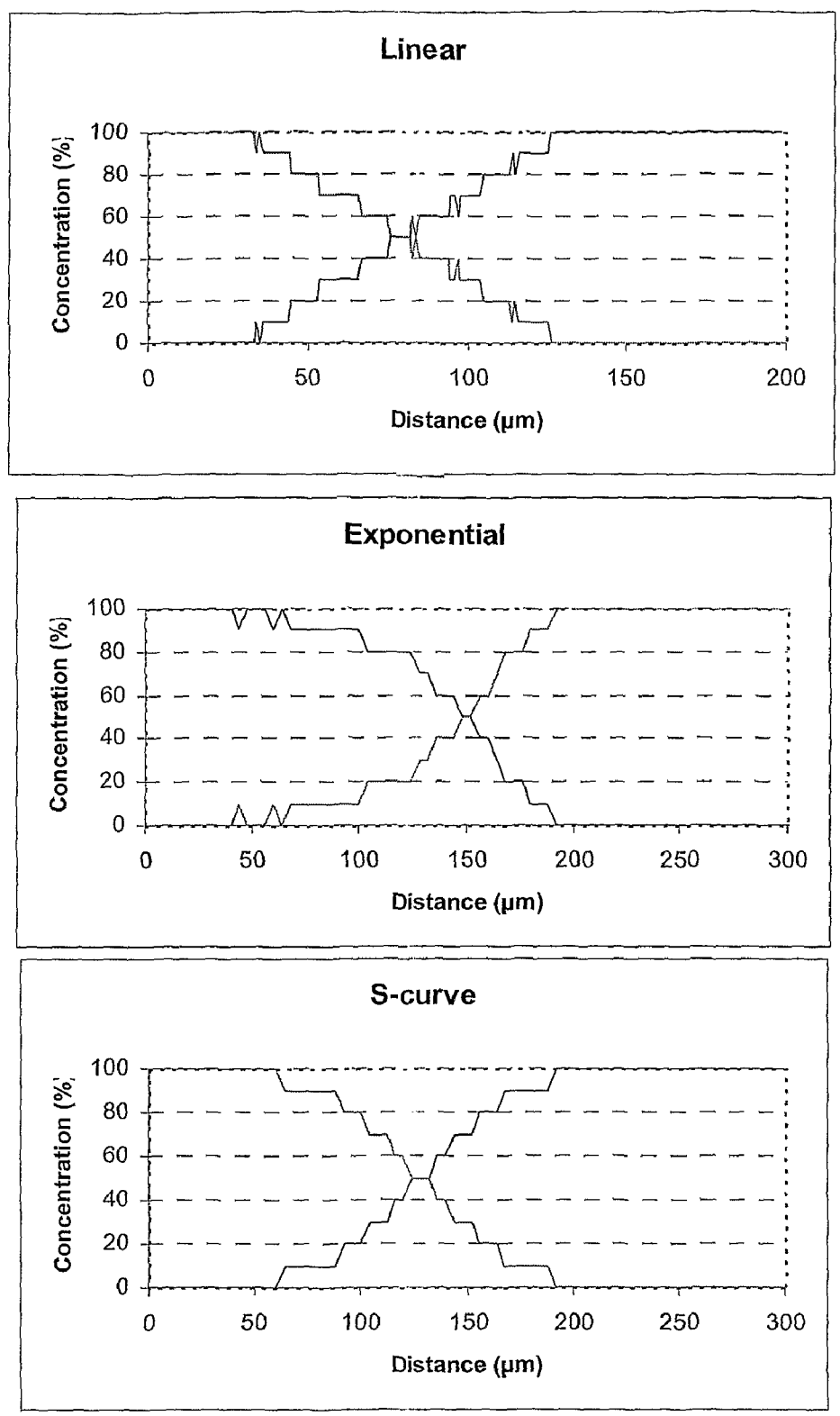

FIG. 4. Examples (a, b and c) of discontinuous gradient polymers.

Figure 5:
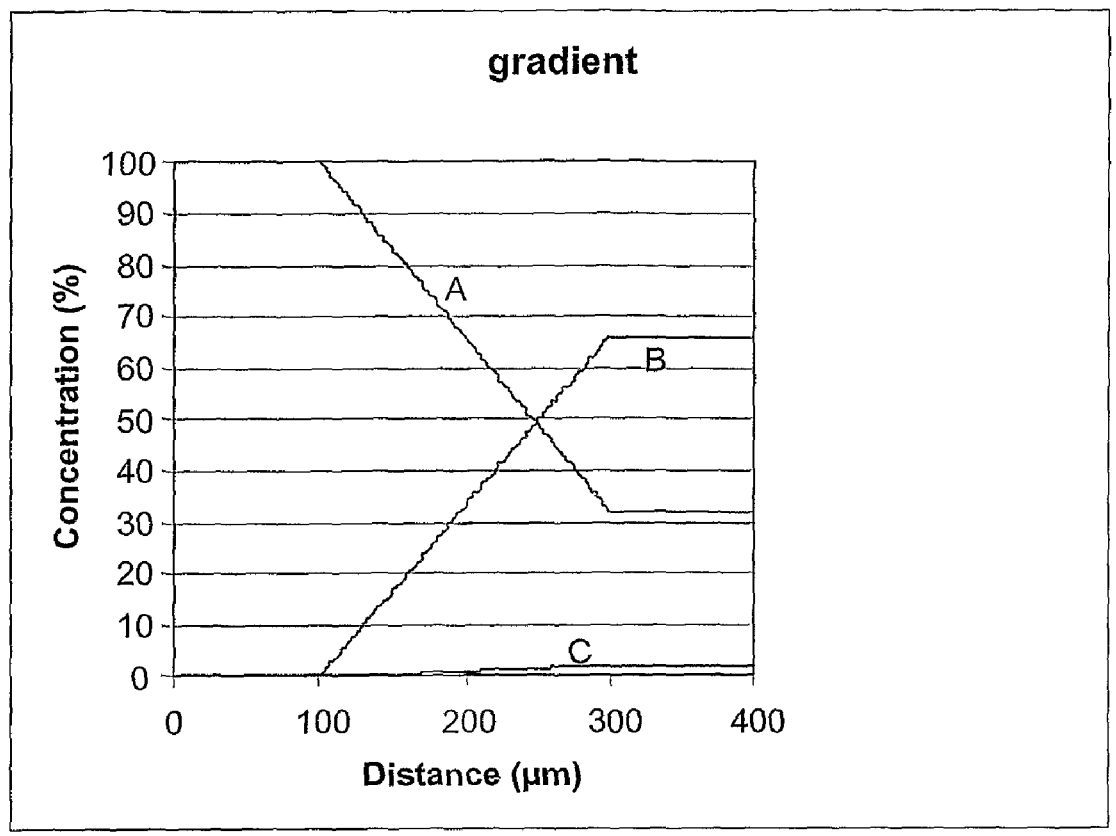

FIG. 5. Gradient of components within a gradient polymer of an electrode from isolator (left) to membrane (right), wherein A is PVC, B is DOS and C is ionophore and ions.

Figure 6:
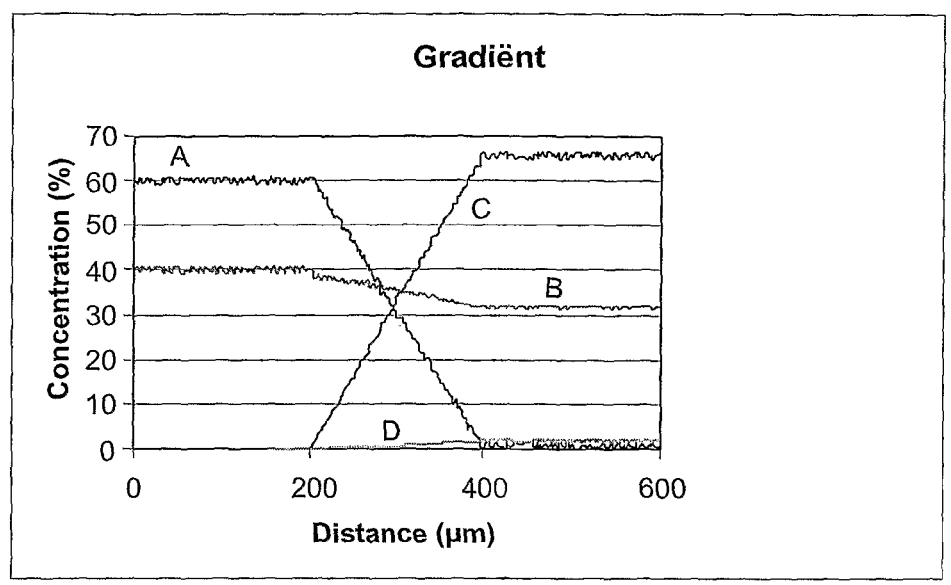

FIG. 6. Gradient of components within a gradient polymer of an electrode from conducting composite (left) to membrane (right), wherein A is graphite, B is PVC, C is DOS and D is ionophore and ions.

Figure 7:
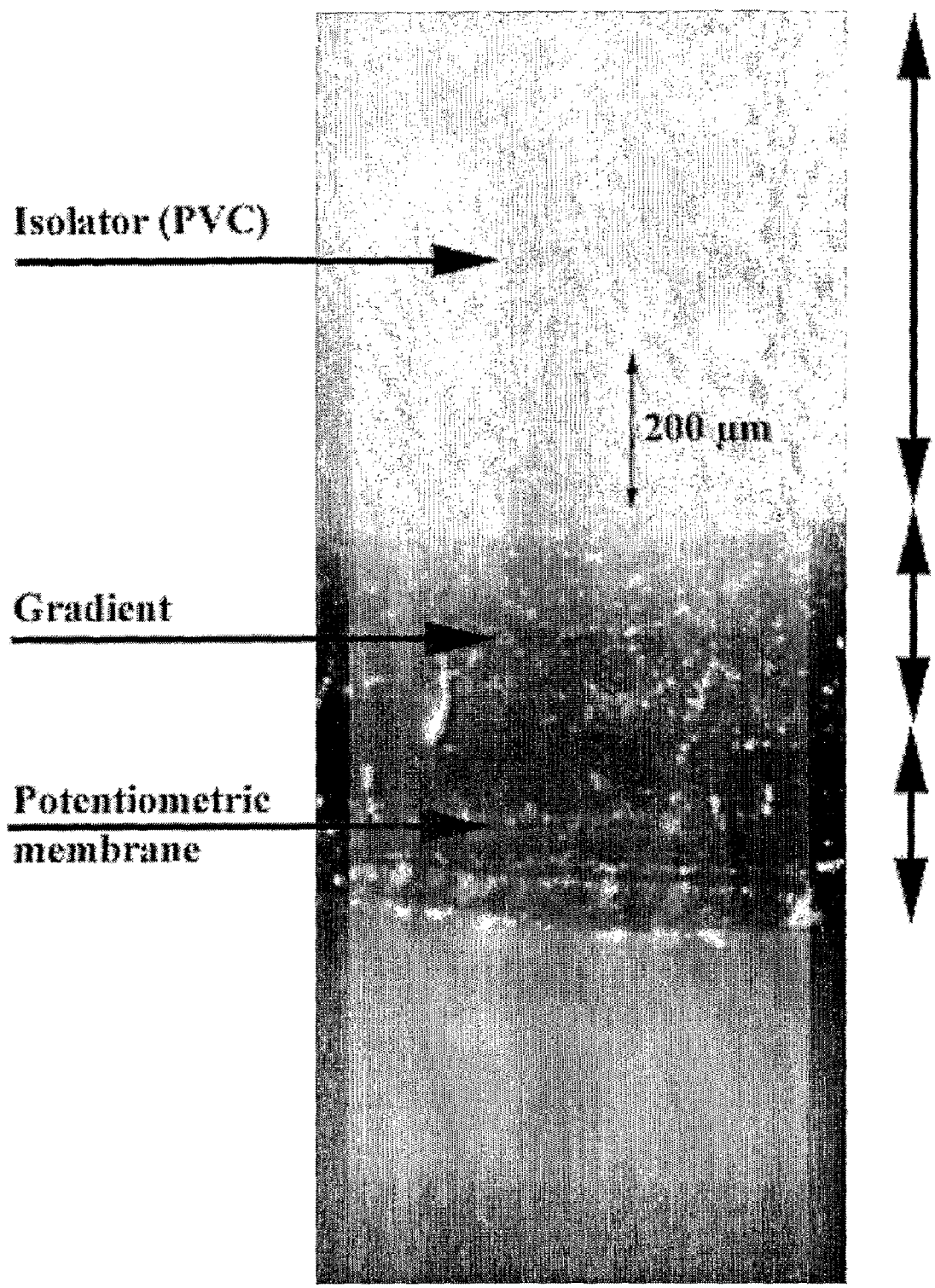

FIG. 7. Photograph of a section of the electrode in reflection microscopy.

Figure 8:
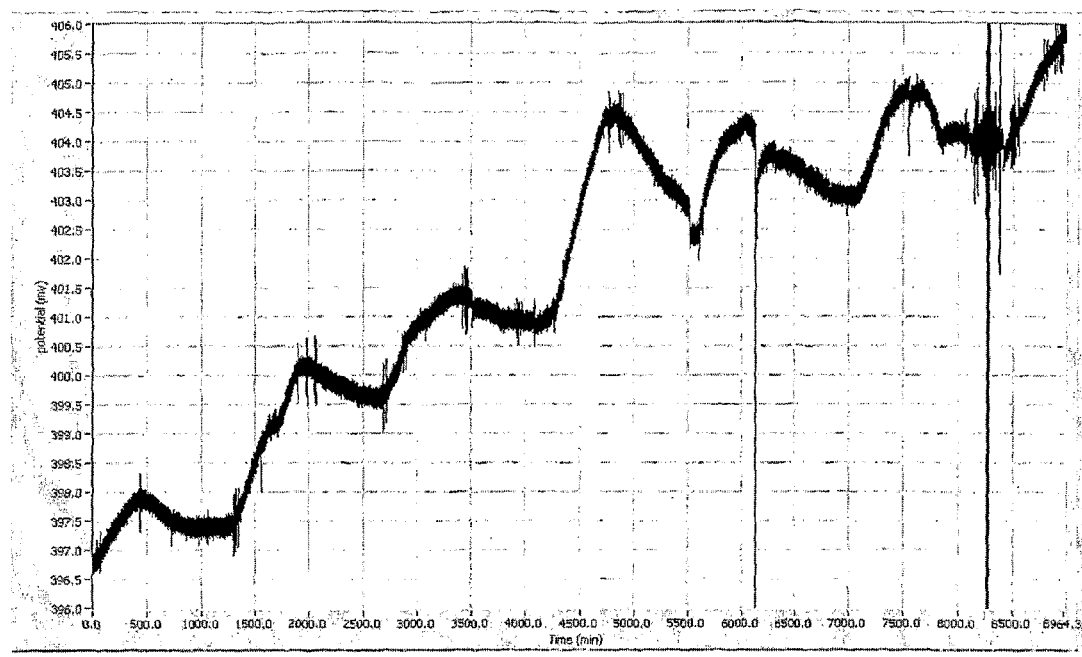

FIG. 8. Drift of an electrode in a 30 mg/l solution of dapoxetine at 37 deg C. over approximately 7 days.

Figure 9:
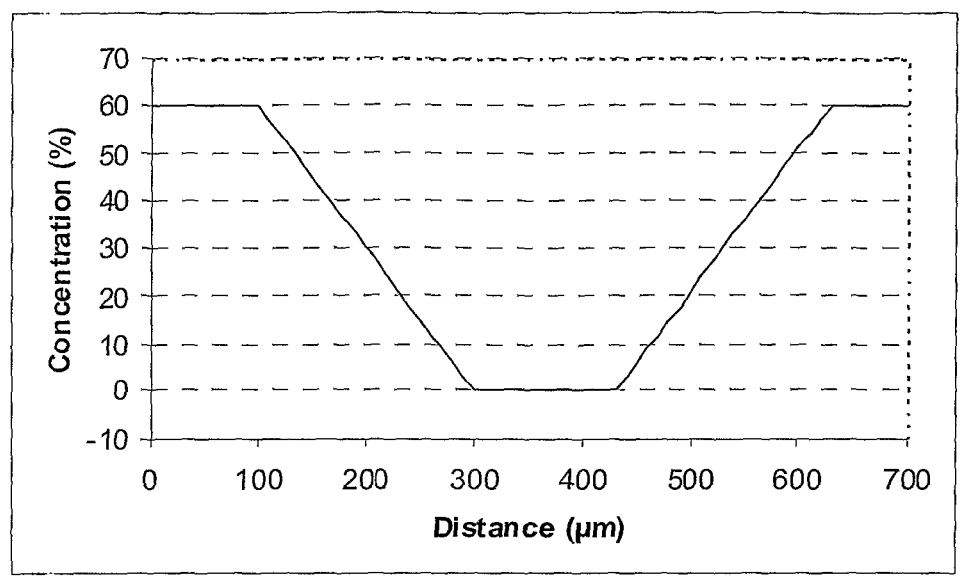

FIG. 9. The graphite concentration in a gradient polymer of two-sided sensor.

Figure 10A:
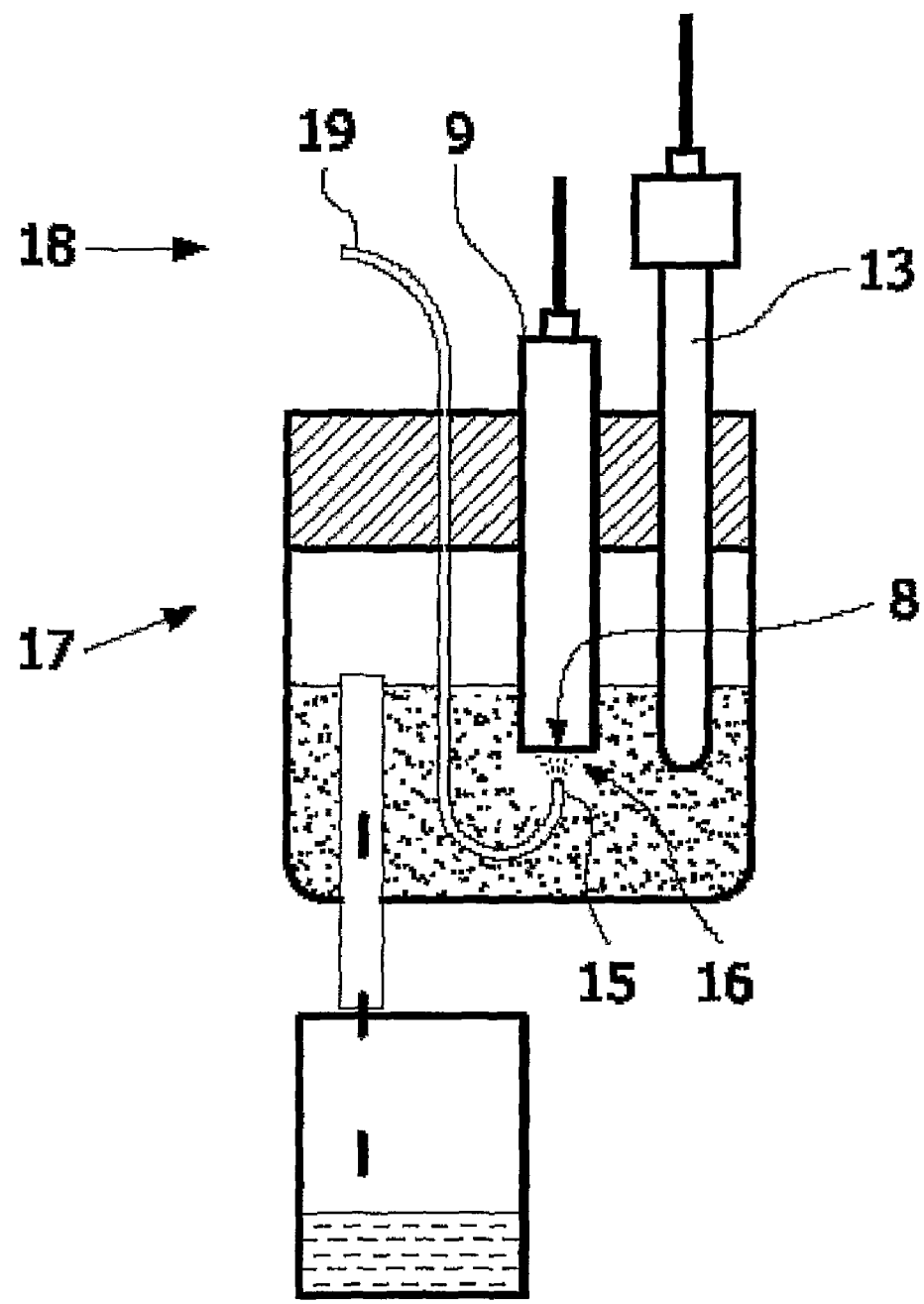
Figure 10B:
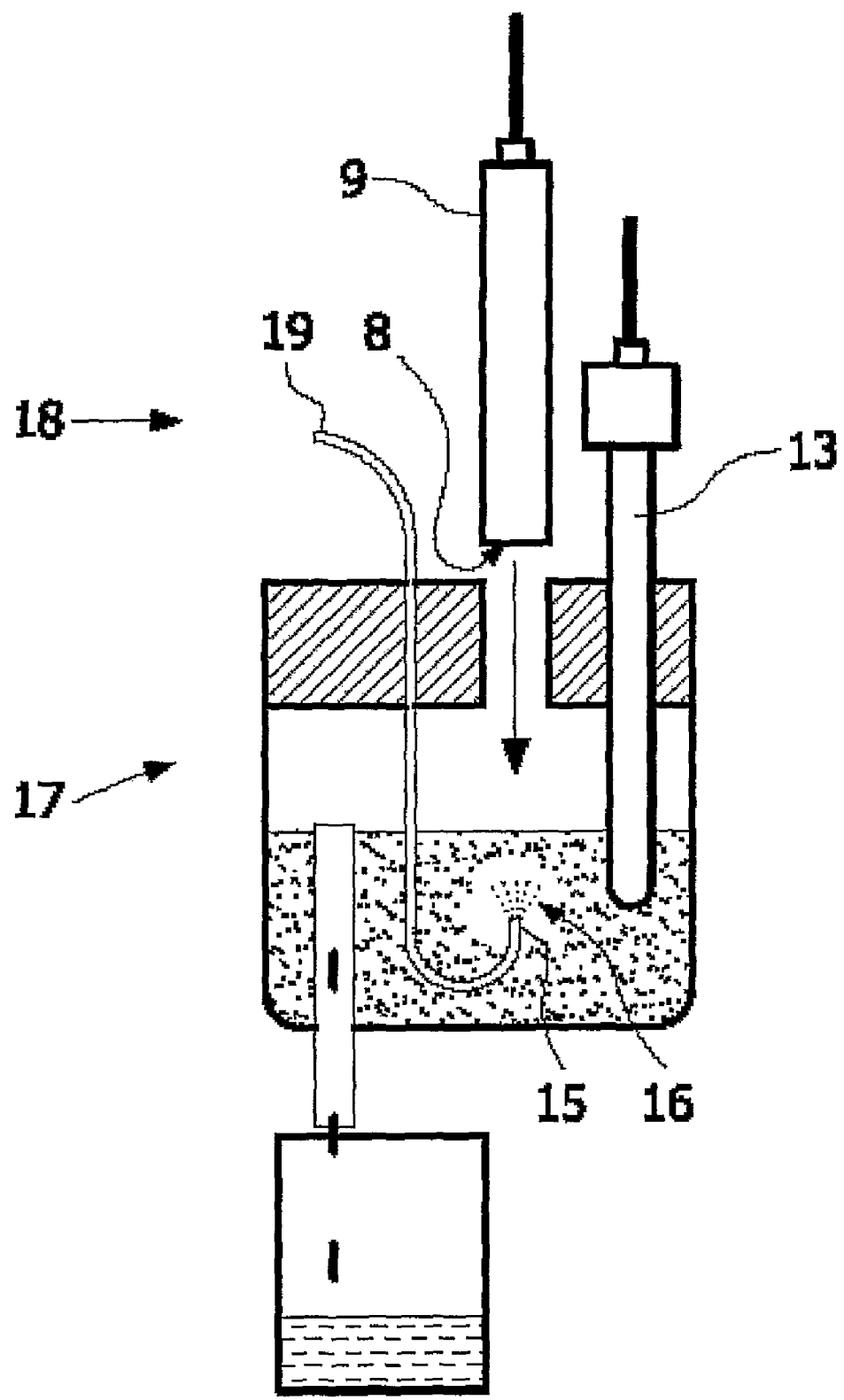

FIGS. 10A and 10B. An example of a flow cell according to the invention.

FIG. 11. Examples of suitable ionophores according to the invention, including compound 11: calix[6]arene, compound 12: calix[4]arene, compound 13: valinomycin, compound 14: nonactin, compound 15: amine ionofore 1, compound 16: dibenzo-18-crown-6, compound 17: Dibenzo-24-crown-8, compound 18: Dibenzo-30 crown-10, compound 19: cyclodextrin, compound 20: phosphoryl derivate, and compound 21 (a crown ether).

Figure 12:
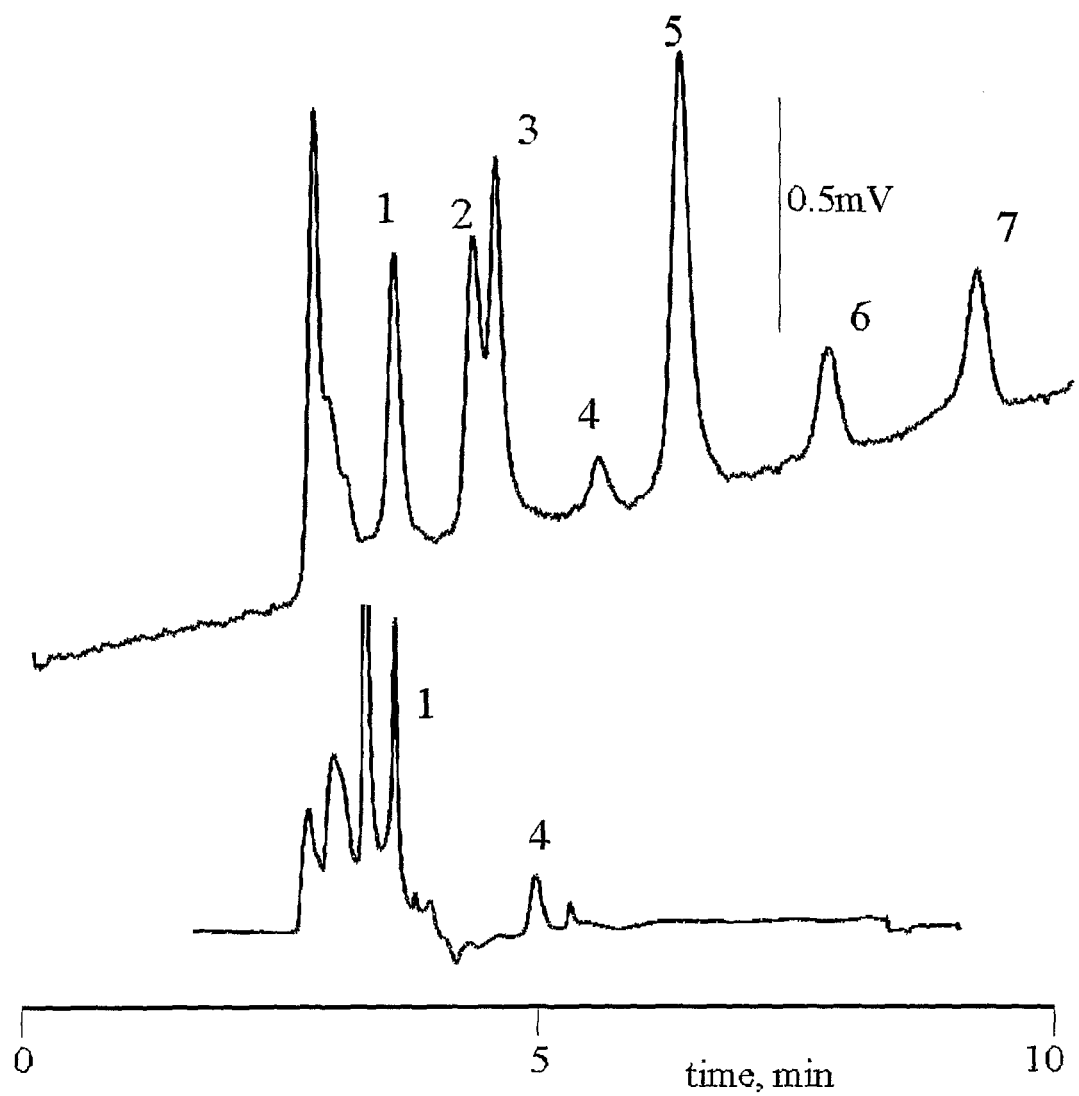

FIG. 12. HPLC traces obtained using an electrode according to the invention based on compound 3. The upper trace shows a chromatogram for the mixture of acids in Table 1. The lower trace presents a chromatogram of an injected beer sample.

Figure 13:
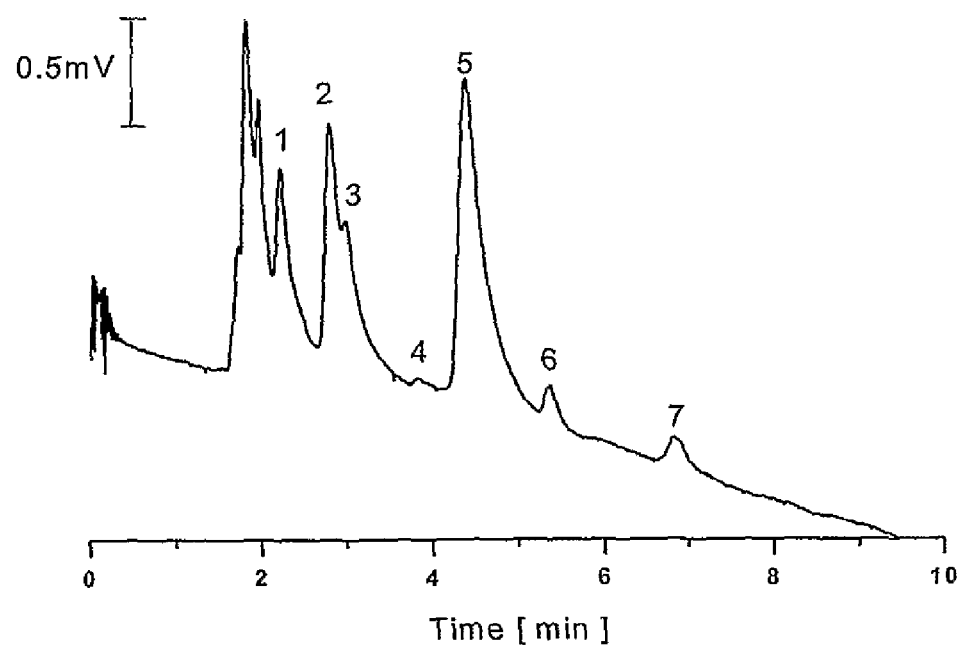

FIG. 13. An HPLC chromatogram recorded with an electrode based on compound 9, with the mixture of acids according to Table 1 as sample.

Figure 14:
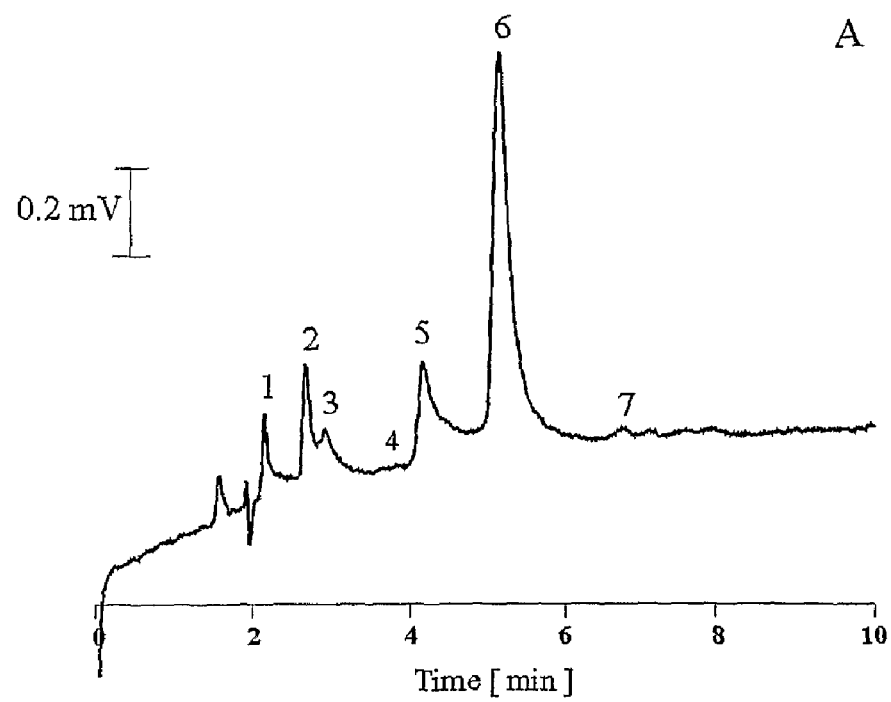
Figure 14:
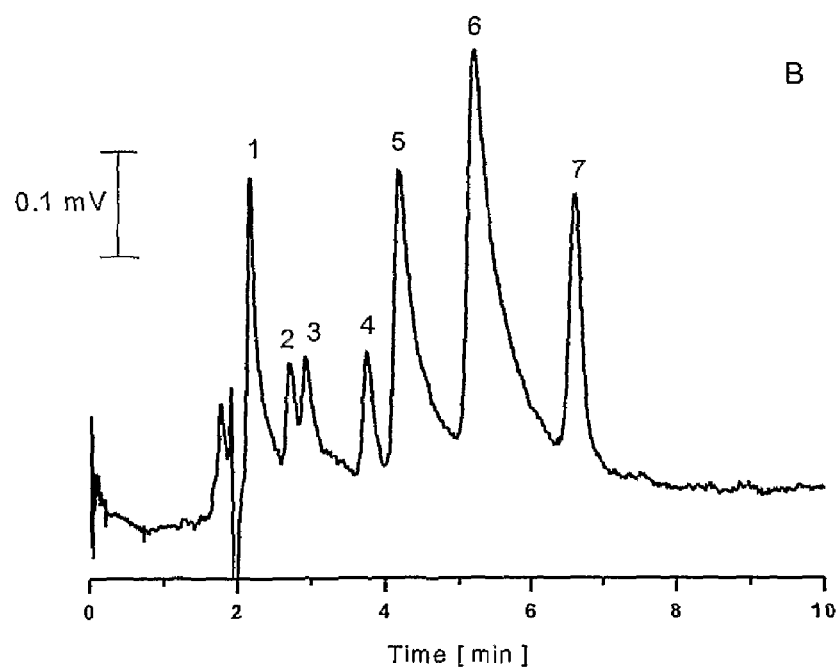

FIG. 14. HPLC chromatograms (A and B) recorded with an electrode based on compound 10, with the mixture of acids according to Table 1 as sample.

Figure 15:
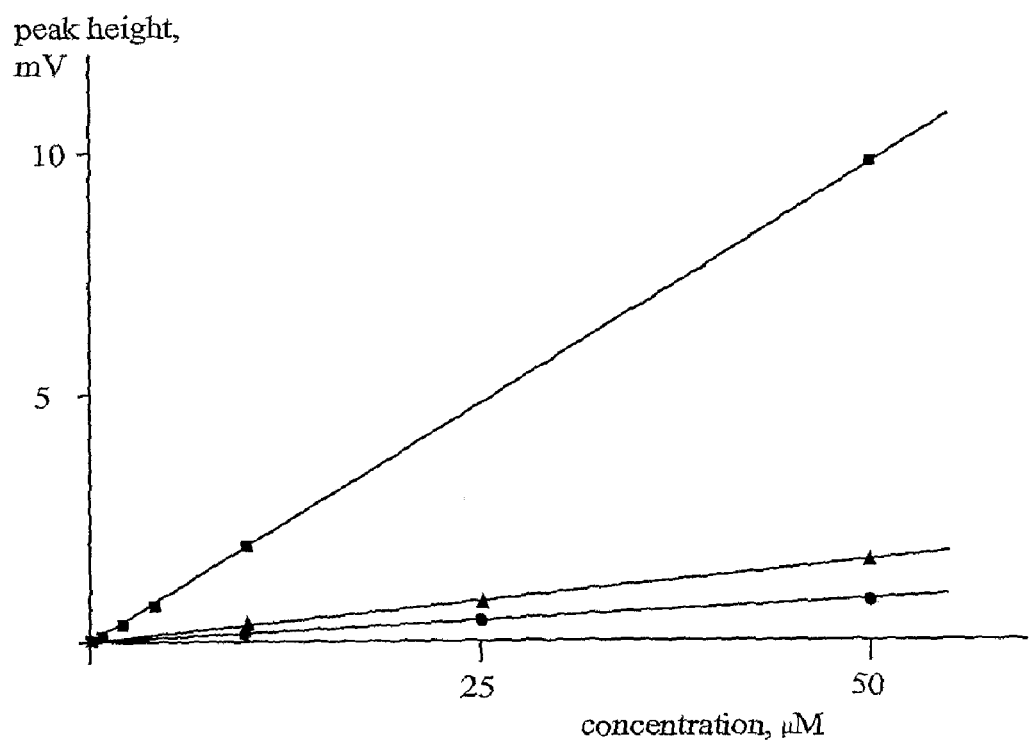

FIG. 15. Calibration curves obtained for three acids in HPLC conditions, with an electrode comprising compound 7.

Figure 16:
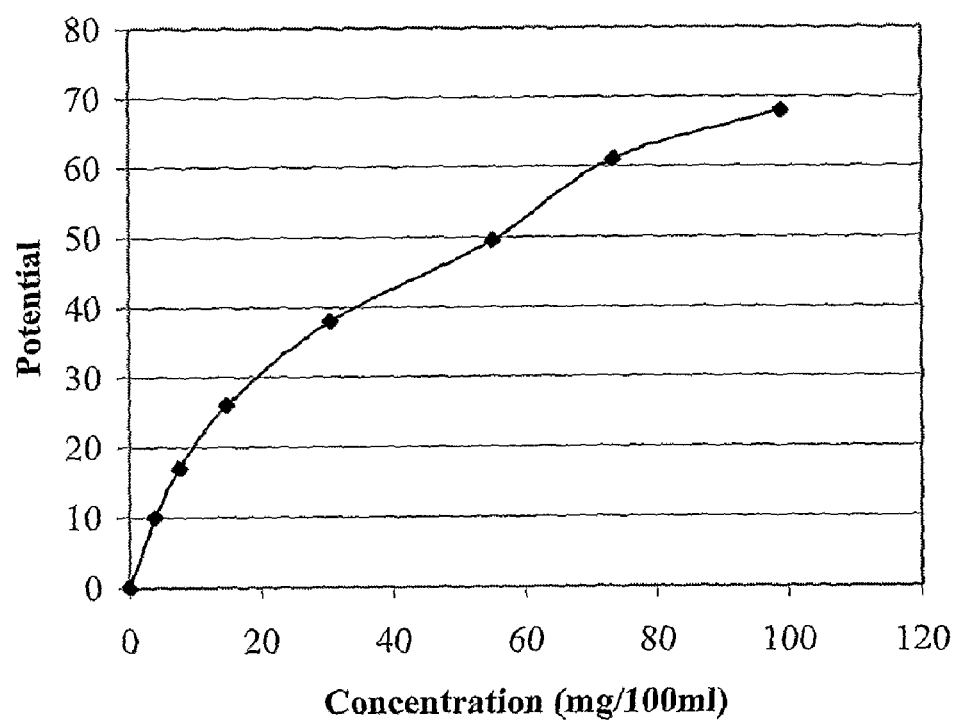

FIG. 16. Curve demonstrating the logarithmic response of an electrode of the invention to concentration in batch conditions.

Figure 17:
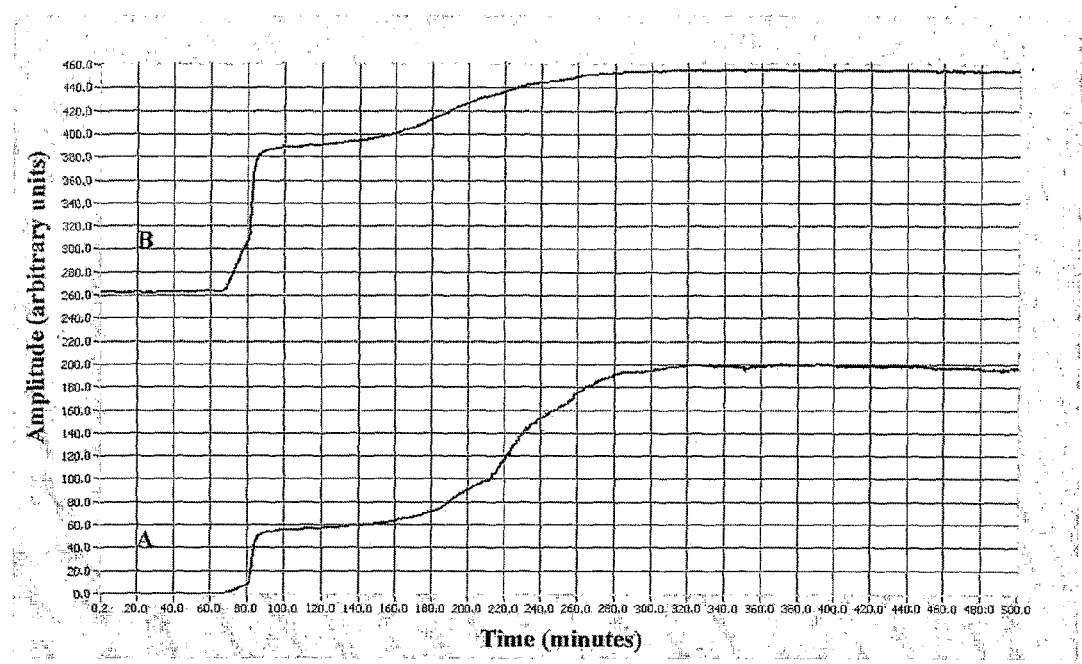

FIG. 17. The monitoring of dissolution of galantamine in HCl using a potentiometric electrode of the present invention.

DETAILED DESCRIPTION OF THE INVENTION

The present invention relates to a potentiometric electrode for detecting analytes in a sample comprising
a sensing body made substantially from polymeric material comprising:
electrically conducting particles, which increase in concentration away from a sample contact surface,
ionophore molecules, which increase in concentration towards the sample contact surface, and
an electrical connection which passes proximal to said electrically conducting particles.

Thus, one embodiment of the present invention is an analyte-selective potentiometric electrode having a sample contact surface, said electrode being substantially formed from polymeric material, said polymeric material comprising:
electrically conducting particles, which increase in concentration away from the sample contact surface,
ionophore molecules capable of binding to said analyte, which increase in concentration towards the sample contact surface, and
an electrical connection which passes proximal to said electrically conducting particles.

Another embodiment of the present invention is a gradient polymer present in an electrode of the present invention.

According to one embodiment of the present invention a gradient polymer is substantially formed from polymeric material comprising two surfaces, said polymeric material comprising:
electrically conducting particles, which decrease in concentration away from one surface,
ionophore molecules which decrease in concentration away from the other surface,
optionally an electrical connection which passes proximal to said electrically conducting particles.

According to one embodiment of the present invention a gradient polymer is substantially formed from polymeric material comprising two surfaces, said polymeric material comprising:
electrically conducting particles, which decrease in concentration away from both surfaces,
optionally electrical connection(s) which passes proximal to said electrically conducting particles.

An electrode or gradient polymer according to the invention, which comprises polymeric material throughout has been found by the inventors to be extremely mechanically robust and sensitive. Furthermore, such an electrode or gradient polymer is suitable for use in HPLC, CE and pharmaceutical applications such as dissolution testing and retains its sensitivity during very long operations. In the area of dissolution testing, the inventors have found that the robust potentiometric electrode performs more reliably than the presently widely used spectroscopic UV fiber-optics sensors. The electrode or gradient polymer does not have a separate and distinct membrane comprising ionophore molecules. Instead, the part of the electrode or gradient polymer comprising ionophore molecules is part of the polymeric material of the body, and the electrode or gradient polymer is one piece. Furthermore, the electrode or gradient polymer is more robust and the inventors have found it is free of abrupt changes in potential which can occur at unpredictable intervals with conventional "coated-wire" electrodes. When it is described that the concentration of a ionophore or electrically conducting particle increases or decreases, it means such change is not abrupt but is gradual or progressive. As elaborated below, the change in concentration of ionophore or electrically conducting particle is a gradient over distance in respect of the longitudinal body or in respect of the sample contact surface. It is mechanically more stable because there is no abrupt interface between the ionically conducting part and the electronically conducting part.

The sensing body of the electrode comprises the gradient polymer, said gradient having a variety of applications including use in a flow cell, a dissolution sensor, battery, variable resistor, variable capacitor, pressure sensor and solvent or lipophilic molecular sensor.

One embodiment of the present invention is an electrode or gradient polymer as disclosed herein wherein the electrical connection is made of any conducting metal such as silver, platinum, gold, aluminium.

Another embodiment the present invention is an electrode or gradient polymer as disclosed herein wherein the electrical connection is made of copper. The use of copper provides good conductivity and is inexpensive. Because an electrode or gradient polymer of the invention can avoid the use of precious metal such as gold, silver or platinum, said electrode provides for a very low cost device.

Another embodiment of the present invention is an electrode or gradient polymer as disclosed herein, wherein polymeric material is any polymeric material which is in the rubber state, or which is brought into this state by the addition of plasticiser. Examples of such materials include poly(n-butylacrylate), poly(butylacrylate), cross-linked poly(butylacrylate), polycarbonate, polystyrene, polymethylmethacrylate, poly(vinylchloride-co-vinylacetate-co-vinylalcohol), polysiloxane, DC 200 silicon oil, polyvinyl chloride (PVC), or high molecular weight PVC or a combination of two or more thereof.

Another embodiment of the present invention is an electrode or gradient polymer as disclosed herein, wherein polymer is polyvinyl chloride (PVC). The inventors have found that PVC provides good strength and is compatible with the electrically conducting particles and ionophores of the electrode or polymer gradient.

Another embodiment of the present invention is an electrode or gradient polymer as disclosed herein, wherein the polymer comprises poly(butylacrylate). The electrode may comprise poly(butylacrylate), or poly(butylacrylate) in combination with PVC. The inventors have found that provides good adhesive properties for the construction of the electrode and is compatible with the electrically conducting particles and ionophores of the electrode.

The region of polymeric material comprising ionophore molecules (FIGS. 1, 11) is also known herein the membrane, while the remainder of the polymeric material (FIGS. 1, 10), which comprises electrically conducting particles is also known as the conducting composite.

According to one aspect of the invention, the membrane region comprises more plasticiser than the conducting composite region. According to this aspect of the invention, the amount of plasticiser in the membrane region is between 40 to 80%, 50 to 70%, 60 to 70%, 60 to 75% and is preferably 66%. According to this aspect of the invention, the amount of plasticiser in the conducting composite region is between 0 to 37%, 0 to 20%, 0 to 10%, and is preferably 0%. According to this aspect of the invention, the plasticiser is any of o-nitrophenyl octyl ether (o-NPOE), dioctyl sebacate (DOS), bis(2-ethylhexyl)phthalate (DOP), tris(2-ethylhexyl)phosphate (TOP) or tris(2-ethylhexyl)trimellitate (TOTM).

According to another aspect of the invention, the membrane region comprises the same polymer as in the conducting composite region. For example, the membrane region and the conducting composite region may both comprise PVC. Alternatively, both regions may comprise poly(butylacrylate).

According to another aspect of the invention, the membrane region comprises one or more polymers different from the conducting composite region. For example, the membrane region may comprise poly(butylacrylate), and the conducting composite region may comprise PVC. Alternatively, the membrane region may comprise a mixture of poly(butylacrylate) and PVC, and the conducting composite region may comprise poly(butylacrylate). Alternatives to poly(butylacrylate) may be employed such as any polymer which has a low glass transition temperature (low Tg) i.e. is in the rubber phase at or below room temperature (below 30, 29, 28, 27, 26, 25, 24, 23, 22, 21, 20 deg C.).

The use of poly(n-butylacrylate) (low Tg) in the conducting composite region provides an ideal self-gluing base for the mounting of the ionophore region.

As used herein for substance amounts, percentages refer to w/w unless otherwise stated.

Another embodiment of the present invention is an electrode or gradient polymer as disclosed herein, wherein the concentration of electrically conducting particles is a gradient across the longitudinal body of the electrode or gradient polymer. The concentration of electrically conducting particles is highest towards one or both surfaces. One aspect of the invention is an electrode or gradient polymer as disclosed herein, wherein the maximum concentration of electrically conducting particles in the conducting composite region is equal to or more than 20, 30, 40, 50, 60, 70, 80 or 90% electrically conducting particles, or a value in the range between any of the two aforementioned percentages. It may be 20 to 90%, 50 to 80%, 60 to 80%, 70 to 80%, 50 to 70%, 60 to 70%, 50 to 60% and is preferably equal to or more than 65% electrically conducting particles.

By proximal in reference to the electrical connection as used herein means the electrical connection passes through a zone of electrically conducting particles. It is an aspect of the invention that the electrical connection passes through a zone of maximum concentration of electrically conducting particles.

The gradient of electrically conducting particles provides a continuous transition between ionic conductivity (low particle concentration) to electronic conductivity (high particle concentration)

Another embodiment of the present invention is an electrode or gradient polymer as disclosed herein, wherein the minimum concentration of electrically conducting particles in the membrane region is equal to or less than 5, 10, 20, 40 or 40% or a value in the range between any of the two aforementioned percentages electrically conducting particles. It may be 0 to 40%, 0 to 30%, 0 to 20%, 0 to 10%, 0 to 5%, 0 to 3% electrically conducting particles, and is preferably 0%.

Another embodiment of the present invention is an electrode or gradient polymer as disclosed herein, wherein the electrically conducting particles are carbon powder, preferably, graphite powder, even more preferably synthetic, with a diameter of 1-2 micrometer. Other electrically conducting particles suitable for use according to the invention include, but are not limited to electropolymerised materials (or any other ion electron converter) such as oxidized polypyrrole and its derivatives, oxidized polythiophenes and polyaniline, noble metals, gold or platinum.

Another embodiment of the present invention is an electrode or gradient polymer as disclosed herein, wherein the electrically conducting particles are of one type (e.g. all graphite powder). Another embodiment of the present invention is an electrode as disclosed herein, wherein the electrically conducting particles are of more than one type. For example, an electrode may comprise electrically conducting particles of graphite powder and gold.

Another embodiment of the present invention is an electrode or gradient polymer as disclosed herein, wherein an ionophore molecule is any molecule suitable for non-covalent binding to the analyte of interest. According to one embodiment of the invention, an ionophore specifically binds to an analyte. According to one embodiment of the invention, an ionophore specifically binds to a group of related analytes. By recognizing one analyte, or a groups of analytes, an ionophore according to the invention enables the specific qualitative and/or quantitative detection of said analytes in the presence of other substances.

An analyte as used herein is the substance of interest which is detectable using an electrode or gradient polymer of the invention. To be useful in the invention, the analyte is ionizable i.e. it can form cations and/or anions. For example, an analyte may be a cation present in a liquid, in a gel, on a surface, in a sample etc. According to the invention, an analyte or a family of related analytes binds specifically to an ionophore present in an electrode or gradient polymer of the invention.

A sample according to the invention is any in which an analyte is capable of being present i.e., in which an analyte is ionisable. A sample may take the form of, for example, a liquid, a vapour, a gel, a vapour, a semi-solid, a liquid film, a moisture film, a suspension, a colloid, an heterogenous mixture, an homologous mixture, etc. Examples of samples include, but are not limited to food-stuffs, drinks, bodily fluids, drinking water, waste water, environmental specimens, chemical-production samples, chemical samples, biological samples etc.

According to one aspect of the invention, the analyte is present as an ion pair in the electrode or gradient polymer, particularly in membrane region.

Ionophores may be any of the art, including tetra(p-chloro) phenylborate (TCPB) for cationic analytes, and methyltridodecylammoniumchloride (MTDDACl) for anionic analytes. Other ionophores are any molecular recognition compound which can be made soluble in the lipophilic electrode material or gradient polymer, and insoluble in a hydrophilic sample. Examples synthesized by applicants for the determination of organic acids are given in FIG. 11. Other ionophores known in the art suitable for use in the present invention include those mentioned in Bühlmann et al. Chemical Reviews 1998 Vol. 98 No 4 p 1650-1687 which is incorporated herein by reference. Other ionophores known in the art suitable for use in the present invention include calixarenes (e.g. FIG. 11 compounds 11, 12 and 15) crown ethers (e.g. FIG. 11 compounds 16, 17, 18 and 21) cyclodextrins (e.g. FIG. 11 compound 19) phosphoryl derivates (e.g. FIG. 11 compound 20) and antibiotics (e.g. FIG. 11 compounds 13 and 14). Improved solubility characteristics may be obtained by incorporating a lipophilic "tail" into the molecular recognition compound.

The sensitivity and selectivity of potentiometric electrodes of the art for the determination of organic ionizable analytes is largely determined by the lipophilicity of the analyte. Best results are obtained with analytes having large positive log P values, wherein P is the distribution coefficient of the analyte over a n-octanol/water two phase system. Most organic acids from the food and drinks industry have low (negative) log P values, and will, therefore, be difficult targets. The inventors have found that a combination of the electrode or gradient polymer as described herein, and a group of urea- or azamacrocycle-based ionophores as shown in FIG. 11 allows the detection of such lipophilic analytes, thereby enabling important analyses to be performed in batch and in HPLC modes.

According to one aspect of the invention, an ionophore is based on a ureum derivative or on an azamacrocycle, and is any selected from the group consisting of compounds 1 to 10 in FIG. 11.

Another embodiment of the present invention is an electrode or gradient polymer as disclosed herein, wherein the concentration of ionophore is a gradient across the longitudinal body of the electrode or gradient polymer. The concentration of ionophore is highest towards one surfaces when a single gradient is present. When two gradient polymers are disposed 'back to back' as mentioned below, the concentration ionophore is highest towards the midpopint. One aspect of the invention is an electrode or gradient polymer as disclosed herein, wherein the maximum concentration of ionophore in the membrane region is 0.1 to 20%, 0.1 to 10%, 0.1 to 9%, 0.1 to 8%, 0.1 to 7%, 0.1 to 6%, 0.1 to 5%, 0.1 to 4%, 0.1 to 3%, 0.1 to 2%, 0.1 to 1%, and is preferably 1%, most preferably 1 to 2% ionophore. For the determination of organic acids, this ionophore is any one of the molecules from FIG. 11. These surface-active receptor molecules largely increase the detectability for organic acids. MTDDACl is added in a 0.2% ratio to obtain good ionic conductivity.

Another embodiment of the present invention is an electrode or gradient polymer as disclosed herein, where the ionophores comprise a single ionophore (e.g. the ionophores are all compound 1 of FIG. 11). Another embodiment of the present invention is an electrode as disclosed herein, wherein the ionophores are an heterogenous mix of at least two ionophores. For example, an electrode may comprise a mixture of compound 1 and 2 shown in FIG. 11.

Another embodiment of the present invention is an electrode or gradient polymer as disclosed herein, wherein the minimum concentration of ionophore in the membrane region is 0 to 0.09%, 0 to 0.08%, 0 to 0.07%, 0 to 0.05%, 0 to 0.025%, and is preferably 0% ionophore.

Another embodiment of the present invention is an electrode or gradient polymer as disclosed herein, wherein the electrical connection does not pass through a zone of ionophore particles.

In another embodiment of the invention, the ionophore molecules and the electrically conducting particles mix in a transition region between the zone of minimum concentration of ionophore molecules and the zone of minimum concentration of electrically conducting particles.

According to an aspect of the invention, the transition region has a depth of less than or equal to 10, 50, 100, 200, 300, 400, 500, 600, 700, 800, 900, 1000 or 3000 micrometers, or a value in the range between any two of the aforementioned depths. The depths may be in the range of 10 to 1000 micrometer, 50 to 500 micrometer, 100 to 400 micrometers, 200 to 300, 100 to 200 and 50 to 100 micrometers and preferably less than or equal to 200 micrometers.

According to another aspect of the invention, the nearest boundary of the transition region is located between 1 and 400, 10 and 400 micrometer, 50 and 300 micrometers, 70 and 200 micrometers and preferably 100 micrometers from the sample contact surface.

In this transition region, a conversion of ionic-to-electronic conductivity takes place more efficiently. According to another aspect of the invention, the depth of the transition region and/or the distance of its boundary from the sample contact surface is such that ionic-to-electronic conductivity takes place efficiently.

The gradient polymer and electrode as described herein, comprises a gradient of electrically conducting particles and ionophores present in the electrode forms a continuous transition from one functional layer to another. This transition can be of any type including linear, exponential or curved as shown in FIGS. 3a, 3b and 3c respectively. The gradient may be continuous. Alternatively, the gradient may not be completely continuous, but may progress in discrete steps (FIG. 4) which follow a linear (FIG. 4a), exponential (FIG. 4b) or S-profile (FIG. 4a), for example. The gradient may be symmetrical or non-symmetrical (e.g. FIG. 5 shows a non symmetrical gradient).

The gradient between the conducting composite and the membrane secures a mechanically strong adherence of the membrane to the conductor. The gradient from the pure composite to the pure membrane spans typically 200 micrometers, but it can vary from 10 to 1000 micrometers. The inventors have observed that branches of composite (graphite/PVC) can extend into the membrane (PVC, DOS and ions). Isolated particles of graphite extend far into the membrane even in regions near to the surface. Due to the extreme low concentration of these particles in these regions, they do not reduce dramatically the impedance of the electrode. A microscopy photograph of the membrane isolator gradient is shown in FIG. 7. From this, the inventors deduced a concentration distribution in the gradient shown in FIG. 6. For this distribution a linear variation of concentration was presumed, however the other presented models could also apply.

Within an electrode or gradient polymer of the present invention, other gradients may be present depending on the material used to make the isolator. Besides the gradient between conducting composite and a gradient membrane, there may be a gradient between the isolator and the membrane and a gradient between the isolator and the conductor. For each of these gradients there may be different gradient profiles for each component.

The gradient between the isolator and the membrane secures a mechanically strong adherence of the membrane to the insulator. Furthermore this gradient has a higher impedance than the membrane and prevents any short-circuit. The gradient from the pure isolator to the pure membrane spans typically 200 micrometers, but it can vary from 10 to 1000 micrometers. From the microscopy photograph of the membrane isolator gradient in FIG. 7 we deduced a concentration distribution in the gradient shown in FIG. 5. For this distribution a linear variation of concentration was presumed, however the other presented models could also apply.

The gradient between the isolator and conducting composite is similar to the previous gradients, and is an unintended result of the electrode production as described above. The gradient may evolve from a graphite concentration equal to or greater than 90, 80, 70, 60, 50, 40, 30, or 20% (or a value in the range between any of the two aforementioned values) to a concentration of 0% in the isolator. The concentration of PVC may evolve from a concentration equal to or less than 10, 20, 30, 40, 50, 60, 70, or 80% (or a value in the range between any of the two aforementioned values) to a concentration equal to or less than 90, 95, or 100% in the isolator. Preferably, the concentration gradient evolves from 60% graphite 40% PVC to 0% graphite 100% PVC. The length of this gradient is smaller, and can vary from 1 to 100 micrometers but can be larger.

In another embodiment of the present invention, the electrode or gradient polymer further comprises a housing (also known herein as an isolator). The housing encloses at least part of a longitudinal body of the polymeric material. The housing leaves the sample contact surface at least partly exposed. Said housing may serve a number of purposes, for example, one or more of the following:

- to physically protect the sensing portion when present in an electrode,
- to provide a reaching means for the sensing portion when incorporated into an electrode,
- to insulate the electrical connection.

The housing may be constructed from any insulating material such as glass, PVC, polycarbonate, polypropylene etc. It is preferably made of PVC. The use of a PVC housing and solvent during preparation of the electrode leads to an isolator-membrane gradient and a isolator conductor composite gradient as described above, owning a solublisation of part of the housing by the solvent.

Another embodiment of the present invention is an electrode or gradient polymer as disclosed herein, wherein the housing is a cylindrical jacket.

In another embodiment of the present invention, the polymeric material is cylindrical in shape.

A cylindrical shape of the electrode or gradient polymer allows an electrode so formed to have an sample contact surface which is circular, so matching the shape of commonly available containers such as micro well plates. Furthermore, this allows the housing of the electrode to be cylindrical, permitting an efficient strength/weight use of housing materials.

In another embodiment of the present invention, the sample contact surface of an electrode, or one or both said surfaces of gradient polymer is circular. The may be between 0.1 and 5 mm, 0.1 and 4 mm, 0.1 and 3 mm, 0.1 and 2 mm, and preferably 3 mm.

The inventors have found that an electrode or gradient polymer of the present invention with the lack of an interface provides a mechanically more robust construction which unexpectedly, has enhanced the sensitivity and conductivity properties which are more predictable in daily use.

Another embodiment of the present invention is a chromatographic flow cell comprising an electrode or gradient polymer of the present invention.

Another embodiment of the present invention is a dissolution electrode comprising an electrode or gradient polymer of the present invention. The inventors have found that a potentiometric electrode made according to the present electrode has a very low drift, and which is predictable (FIG. 8). These properties allow measurements to be made inline—i.e. the electrode registers continuously and in real time the concentration changes of the dissolution media; the electrode does not leave the dissolution media during dissolution. This contrasts to potentiometric electrodes of the prior art in which samples are taken out and measured, or the electrode is intermittently introduced into the dissolution solution.

Besides the normal calibration curves, additional calibration techniques can be applied to the present electrode or gradient polymer. The measurement of the end concentration is very sensitive to drift; this problem can be suppressed by single point calibration or standard addition. Single point calibration usually performed soon after completion of the dissolution by placing the electrode in a known concentration of analyte. This enables the correction of the calibration values for the occurred drift by simple subtraction and interpolation. A known amount of analyte may also be added after completion of the dissolution (standard addition). Since the increase in voltage is proportional to the start concentration and the amount added, the end concentration can be deduced. This also enables the calibration values to be corrected for the occurred drift by simple subtraction and interpolation.

Another embodiment of the present invention is a chromatographic flow cell as disclosed herein, further comprising a means to spray eluent against the electrode or gradient polymer surface. Said configuration is a so called "walljet".

The inventors have found that a flow cell according to the invention obviates the main problem with classical flow-cells which is the unpredictable occurrence of high internal resistances. These come from air bubbles sticking to the working electrode, or from reference electrodes with clogged membranes. Both causes are difficult to detect in classical flow cells. Classical cells have to disassembled, and even then, the cause of misfunction is not evident. Furthermore, re-assembling the flow-cell will generally not remove the problem. The latter phenomena make present electrochemical detection impractical for users. The inventors have found that no such phenomena occur with the flow-cell of the present invention. A flow cell according to the invention operates at zero pressure, allows immediate visual inspection of air bubble formation at the electrode, and convenient and effective removal of such in seconds. The reference electrode can also be removed in seconds time. The construction of the flow-cell is such that an industrial standard reference electrode can be plugged in—no specially constructed reference electrode is needed.

The gradient polymer described herein may comprise two surfaces and a longitudinal body. A cylinder, for example, comprising two circular ends and a longitudinal body is a typical shape of construction of gradient polymer. The gradient polymer as already described above may comprise electrically conducting particles increasing in concentration towards one surface, and ionophore molecules increasing in concentration towards the other surface. A gradient polymer may also comprise two surfaces in which electrically conducting particles decrease in concentration towards the midpoint of both surfaces.

The gradient polymer can be implemented into a device wherever a transition between ionic and electrical conductivity is needed. A gradient polymer may thus be implemented, for example, into batteries.

It may also be implemented as a variable resistor or variable capacitor. In this construction the component is essentially two gradients 'back to back', in which electrically conducting particles decrease in concentration towards the midpoint of both surfaces. The end surfaces of the components comprise a maximum concentration of electrically conducting particles, which reduce in concentration towards the centre (midpoint) of the component. For example, the gradient may run from one end from 60% graphite to 0% graphite in the centre and increases back to 60% at the other end, this profile being shown in FIG. 9). The central area may be in the rubber phase at or below room temperature and may contain ions and/or ionophores.

The gradient polymer may also be implemented into a pressure sensor. For such sensor, again two 'back to back' gradients are formed in which electrically conducting particles decrease in concentration towards the midpoint of both surfaces. For example, the gradient may run at one end from 40% PVC 60% graphite to 66% DOS, 44% PVC, 0% graphite in the centre (midpoint) to 40% PVC 60% graphite at the other end. When this gradient is compressed, the capacitance and conductivity varies in proportion to the pressure applied. Hence, a capacitance and/or impedance based pressure sensor is obtained. Ionphores may be present or absent in the central area.

The gradient polymer as described in the above embodiments may also by implement into a solvent or lipophilic molecular sensor. Such sensor based on the swelling properties of the gradient. Many solvents become trapped in the gradient polymer and cause swelling of the rubber phase. This characteristic affects the conductivity and capacitance of the sensor. Both properties can be used to determine the solvent concentration. The same system can be used for measurement of detergents and molecules with high log P (>1). These molecules can be in the solution or gas phase.

Method of Preparation

The potentiometric electrodes and gradient polymers can be prepared using the methods described below. The methods are directed towards the construction of the electrode, however, the essential steps are described for forming the gradient polymer. The skilled person may adapt the described methods within his skill to prepare the gradient polymers.

Another embodiment of the present invention is a method for making a potentiometric electrode as described herein comprising the steps of:

(a) preparing a suspension of electrically conducting particles in a solution of polymer in a solvent, (b) inserting an electrical conductor therein, (c) drying the suspension, so forming a solid composite polymer with electrically conducting particles therein, (d) adding, to a surface of the particle/polymer composite, a solution of polymer, electrically conducting particles, and ionophore.

(e) drying the mixture.

(f) repeating steps (d) and (e), with decreasing concentrations of electrically conducting particles, and increasing concentrations of ionophore, and (g) obtaining a potentiometric electrode with composite gradient properties and no interfaces.

Another embodiment of the present invention is a method for making a potentiometric electrode as described herein comprising the steps of:

(a) preparing a suspension of electrically conducting particles in a solution of polymer in a solvent, (b) inserting an electrical conductor therein, (c) drying the suspension, so forming a solid composite polymer with electrically conducting particles therein, (d1) adding, to a surface of the particle/polymer composite, a solution of polymer and ionophore.

(e1) drying the mixture.

(f1) repeating steps (d1) and (e1), and (g1) obtaining a potentiometric electrode with composite gradient properties and no interfaces.

Another embodiment of the present invention is a method for making a potentiometric electrode as described herein comprising the steps of:

(a1) preparing a suspension of electrically conducting particles in a solution of polymer in a solvent, (b1) injecting the suspension into distilled water, so forming a precipitate, (b2) reducing the size of the precipitate to form a residue, (c1) drying the residue by pressing to form a conducting particle/polymer composite, followed by steps (d) to (g) or (d1) to (g1) mentioned above After hydration, the electrode is ready to be used.

The potentiometric electrode formed by the method is constructed from a continuous polymer throughout the electrode, so providing the electrode with an unexpected durability, toughness and sensitivity. The electrode also has no interfaces, and so its enhanced sensitivity and conductivity properties are more predictable in daily use The properties and variations of the polymeric material, ionophore, electrically conducting particles and electrical conductors are the same for the method as for the electrode or gradient polymer discussed above.

One embodiment of the invention is a method as disclosed herein, wherein the suspension of step (a) is poured into a cylindrical mold. This allows the electrode so formed to have an sample contact surface which is circular, so matching the shape of commonly available containers such as micro well plates. Furthermore, this allows the housing of the electrode to be cylindrical, permitting an efficient strength/weight use of housing materials. According to an aspect of the invention, the mold may be the housing of the electrode.

The suspension of step (a) may be provided to the mold in one single application, or by consecutive rounds of applying and drying until the desired amount of suspension has been added. The drying may be performed at room temperature or elevated temperature (e.g. higher than 20, 25, 30, 35, 40, 45, 50, 55, 60, 65, 70, 75, 80, 85 or 90 deg C., or a value in the range between any of the two aforementioned temperatures). After the desired amount of composite has been added and the suspension dried, the surplus composite may be removed by grinding and polishing.

According to the present invention, the suspension of step (a) or (a1) comprises electrically conducting particles (e.g. graphite) and polymer in solvent. The relative proportion (w/w) of electrically conducting particles to polymer is 20, 30, 40, 50, 60, 70, 80, 90% graphite, or a value in the range between any of the two aforementioned percentages, the remainder being made to 100% with the appropriate mass of polymer. The preferred proportion of electrically conducting particles is 50 to 70%, more preferably 55 to 65%, most preferably 60%, the remainder being made to 100% with polymer.

Similarly, the relative proportion (w/w) of polymer to electrically conducting particles in the suspension of step (a) or (a1) is 10, 20, 30, 40, 50, 60, 70, 80, % graphite, or a value in the range between any of the two aforementioned percentages. The preferred proportion of polymer is 20 to 50%, more preferably 30 to 40%.

Examples of suitable polymers include poly(n-butylacrylate), poly(butylacrylate), polycarbonate, polystyrene, polymethylmethacrylate, poly(vinylchloride-co-vinylacetate-co-vinylalcohol), polysiloxane, DC 200 silicone oil and preferably high molecule weight polyvinyl chloride (PVC).

The proportion of solid to solvent in the solution of step (a1) may be one part solid components (electrically conducting particles+polymer) to less than 1, 2, 3, 4, 5, 6, 7, 8, 9, 11, 12, 13, 14, 15, 16, 17, 18, 19, 20, 21, 23, 24, 25, 26, 27, 28, 29, 30, 40, 50, 60 parts solvent, or a value in the range between any of the two aforementioned values. The preferred ratio (w/v) of solid components (electrically conducting particles+polymer) to solvent is 1:(1 to 10), more preferably 1:(1 to 5), most preferably about 1:3.

The solvent used in the method of the present invention is any that dissolves the polymer. Such solvents are known in the art, and includes DMSO, 111 trichloroethane, $CCl_4$, N,N-dimethylformamide and N,N-dimethylacetamide, and THF.

Another embodiment of the invention is a method as disclosed herein, wherein the solution of step (d) or (d1) (and (f)) further comprises plasticiser. According to a method of the invention, the amount of plasticiser in the polymeric material of the ionophore-containing region is between 40 to 80%, 50 to 70%, 60 to 70%, 60 to 75% and is preferably 66%. 50 to 75%, 55 to 75%, 60 to 75%, 65 to 75%, 50 to 70%, 50 to 65%, 50 to 60 and preferably 66% plasticiser. According to this aspect of the invention, the amount of plasticiser in the remainder of the polymeric material (conducting composite) is between 0 to 37%, 0 to 20%, 0 to 10%, and is preferably 0%.

Another embodiment of the invention is a method as disclosed herein, wherein the solution of step (d) or (d1) (and (f)) further comprises ionophore. According to a method of the invention, the maximum concentration of ionophore in the electrode is equal to or less than 0.1, 0.25, 0.5, 0.75, 1, 1.5, 2, 2.5, 3, 4, 5, 6, 7, 8, 9 or 10% w/w in the membrane region. It may be between 0.1 and 10%, 0.1 and 9%, 0.1 and 8%, 0.1 and 7%, 0.1 and 6%, 0.1 and 5%, 0.1 and 4%, 0.1 and 3%, 0.1 and 2%, 0.1 and 1%, and is preferably less than or equal to 1% ionophore.

Another embodiment of the invention is a method as disclosed herein, wherein the solution of step (d) or (d1) and (f) further comprises polymer. According to a method of the invention, the maximum concentration of polymer in the membrane region of the electrode is between 20 and 45%, 20 and 40%, 20 and 35%, 20 and 30%, 25 and 45%, 30 and 45%, 35 and 45%, and is preferably 33%.

According present method, the solution of step (d1) may comprise polymer and ionophore and no electrically conducting particles. Said solution is applied to the composite of step (c) or (c1) by consecutive applications (step (f1)). The inventors have found that a gradient of ionophore particles increasing in the direction towards the sample contact surface, and a gradient of electrically conducting particles decreasing in concentration in the direction towards the sample contact surface is surprisingly formed, without changing the composition of the solution mentioned in step (d1) between consecutive additions. The gradient is formed by the dissolving of the composite of step (c) or (c1) by the solution of step (d1). Using this procedure, one obtains a gradient layer (transition region) of between 10 and 1000 micrometers in depth.

Depending on the volume of solution applied in step (d1), the depth of transition region can be adjusted. It can generally be less than 1, 10, 50, 70, 90, 100, 150, 190, 200, 210, 250, 300 micrometers in depth, or a value in the range between any of the two aforementioned depths, preferably 150 to 250 micrometers, and most preferably about 200 micrometers.

The volume of solution applied in step (d1) may be less than 5, 10, 15, 20 25, 30, 35, 40, 45 or 50 microliters, or a value in the range between any of the two aforementioned volumes. It is preferably between 15 and 35 microliters, more preferably between 20 and 30 microliters and most preferably about 25 microliters.

According to one aspect of the invention, the solution of step (d1) comprises plasticiser, polymer and ionophore in solvent (e.g. THF). The composition of the membrane components (plasticiser+polymer+ionophore), may comprise more than 0, 1, 10, 20, 30, 40, 45, 50, 55, 60, 65, 70, 75, 70, 75 or 80% plasticiser or a value in the range between any of the two aforementioned percentages, preferably 55 to 75%, more preferably 60 to 70% and most preferably about 65% plasticiser. The plasticiser may be any of the art, including o-nitrophenyl octyl ether (o-NPOE), dioctyl sebacate (DOS), bis(2-ethylhexyl)phthalate (DOP), tris(2-ethylhexyl)phosphate (TOP) or tris(2-ethylhexyl)trimellitate (TOTM), but is preferably DOS.

The composition of the membrane components (plasticiser+polymer+ionophore) in the solution of step (d1), may comprise less than 20, 22, 24, 26, 28, 30, 32, 33, 34, 36, 38, 40, 42, 44, 46, 50, 60, 70, 80, 90, 100% polymer or a value in the range between any of the two aforementioned percentages, preferably 28 to 38%, more preferably 32 to 34% and most preferably about 33% polymer. The polymer comprises the same polymer used in steps (a) to (c) or (a1) to (c1) described above.

The composition of the membrane components (plasticiser+polymer+ionophore) in the solution of step (d1), may comprise less than 0.1, 0.25, 0.5, 0.75, 1, 1.5, 2, 2.5, 3, 4, 5, 6, 7, 8, 9 or 10% ionophore or a value in the range between any of the two aforementioned percentages, preferably 0.1 to 3%, more preferably 0.5 to 2.5% and most preferably 1 to 2% ionophore. The ionophore may be any of the art, depending on the desired application, including tetra(p-chloro)phenylborate (TCPB) for cationic analytes, or methyltridodecylammoniumchloride (MTDDACl) for anionic analytes or any of those listed in FIG. 11.

The proportion of solvent (e.g. THF) in the solution of step (d1) may be one part membrane components (plasticiser+polymer+ionophore) to less than 5, 6, 7, 8, 9, 11, 12, 13, 14, 15, 16, 17, 18, 19, 20, 21, 23, 24, 25, 26, 27, 28, 29, 30, 40, 50, 60 parts solvent, or a value in the range between any of the two aforementioned values. The preferred ratio (w/v) of membrane components (plasticiser+polymer+ionophore) to solvent is 1:(8 to 12), more preferably 1:(9 to 11), most preferably about 1:10.

The composition of membrane components (plasticiser+polymer+ionophore) may vary within the above mentioned limits. The skilled person would use his normal judgment to prepare a composition, where necessary adjusting the relative proportions of membrane components to obtained the desired composition.

According to one aspect of the invention, the solution of step (d1) comprises polymer and ionophore in solvent (e.g. THF), and no plasticiser. The composition of the membrane components (said polymer+said ionophore), may comprise less than or equal to 70, 75, 80, 85, 90, 95, 96, 97, 98, 99% polymer or a value in the range between any of the two aforementioned percentages, preferably 85 to 99%, more preferably 90 to 99% and most preferably less than or equal to 98% polymer. The polymer is any having a Tg (glass transition temperature) below room temperature e.g. polysiloxane or preferably poly(butylacrylate).

The composition of the membrane components (polymer+ionophore) in the solution of step (d1), may comprise less than 0.1, 0.25, 0.5, 0.75, 1, 1.5, 2, 2.5, 3, 4, 5, 6, 7, 8, 9 or 10% ionophore or a value in the range between any of the two aforementioned percentages, preferably 0.1 to 3%, more preferably 0.5 to 2.5% and most preferably 1 to 2% ionophore. The ionophore may be any of the art, depending on the desired application, including tetra(p-chloro)phenylborate (TCPB) for cationic analytes, or methyltridodecylammoniumchloride (MTDDACl) for anionic analytes.

The composition of membrane components (polymer+ionophore) may vary within the above mentioned limits. The skilled person would use his normal judgment to prepare a composition, where necessary adjusting the relative proportions of membrane components to obtained the desired composition.

It is an aspect of the invention that the polymer used in steps (a) or (a1) and (d) or (d1) (and (f)) when plasticiser is absent, is the same, and is any having a Tg (glass transition temperature) below room temperature e.g. poly(butylacrylate) or polysiloxane. It is also an aspect of the invention that the polymers used in steps (a) or (a1) and (d) or (d1) and (f) when plasticiser is absent, are different. The polymer of steps (a) or (a1) may be any of poly(n-butylacrylate), polycarbonate, polystyrene, polymethylmethacrylate, poly(vinylchloride-co-vinylacetate-co-vinylalcohol) and preferably polyvinyl chloride (PVC), the polymer of steps (d) or (d1) and (f) may be poly(butylacrylate), polysiloxane or any polymer having a Tg (glass transition temperature) below room temperature.

In this embodiment the proportion of solvent in the solution of step (d1) may be one part membrane components (polymer+ionophore) to less than 5, 6, 7, 8, 9, 11, 12, 13, 14, 15, 16, 17, 18, 19, 20, 21, 23, 24, 25, 26, 27, 28, 29, 30, 40, 50, 60 parts solvent, or a value in the range between any of the two aforementioned values. The preferred ratio (w/v) of membrane components (polymer+ionophore) to solvent is 1:(8 to 12), more preferably 1:(9 to 11), most preferably about 1:10.

The number of repetitions performed in step (f) and (f1) can very according to the desired gradient profile, transition depth and volume of solution applied in step (d) or (d1). The number of repetitions may be less than 2, 3, 4, 5, 6, 7, 8, 9, 10, 11, 12, 13, 14, 15, 16, 17, 18, 19, 20 or a value in the range between any of the two aforementioned values. The preferred number of repetitions may be between 1 and 10, more preferably between 1 and 7 and most preferably between 1 and 3.

After hydration, the electrode is ready to be used.

According to one aspect of the invention, the analyte is present as an ion pair in the electrode, particularly in the membrane region. In order to obtain this ion pair, the following procedures may be used:

The ion pair (or analyte) may introduced by adding it to the membrane components during fabrication (e.g. adding to the solution of step (c) or (c1).

The ion pair may formed by direct contact of the finished electrode with a solution of the analyte (e.g. 30 mg dapoxetine in a 900 ml solution of 0.1M HCl). During this process, the analyte is extracted from the solution into the electrode, and the ion pair is formed in situ. The process may take up to 5 hours.

In another embodiment of the present invention, an electrode comprising a polysiloxane membrane is constructed as follows:

a3) preparing a paste comprising:
   a suspension of electrically conducting particles used in step (a) or step (a1) above, with or without solvent, or
   a suspension of electrically conducting particles used in step (a) or step (a1) above, with or without solvent, in which the polymer is polysiloxane, or
   a suspension of electrically conducting particles used in step (a) or step (a1) above, with or without solvent, in which the polymer is DC 200 silicon oil, b3) inserting an electrical conductor therein, c3) adding to a surface of the particle/polymer composite a mixture comprising base, curing agent, ionophore, optionally dissolved in solvent (e.g. THF), d3) degassing the construction, e3) heating the construction, and f3) obtaining a potentiometric electrode with composite gradient properties and no interfaces. After hydration one obtains a working electrode.

Base and curing agents are components known in the art and may be any suitable for use in polymerisation. They are preferably components of Sylgard 184 (Dow Corning)

In this embodiment the proportion of optional solvent (e.g. THF) in the solution of step (c3) may be one part solid mixture to less than 0.1, 0.2, 0.3, 0.4, 0.5, 0.7, 0.8, 0.9, 1, 2, 3, 4, 5, 6, 7, 8, 9, 11, 12, 13, 14, 15, 16, 17, 18, 19, 20, 21, 23, 24, 25, 26, 27, 28, 29, 30, 40, 50, 60 parts THF, or a value in the range between any of the two aforementioned values. The preferred ratio (w/v) of solid components to solvent is 1:(0.1 to 1), most preferably about 1:0.5.

The construction may be heating in step e3) to an temperature equal to or greater than 50, 60, 70, 80, 90, 100, 110, 120, 130, 140, 150, 160, 170, 180, 190, 200, 210, 220, 230, 240, 250 deg C., or a value in the range between any of the two aforementioned temperatures. Preferably, the temperature is 100 to 250 deg C., more preferably, 130 to 220 deg C., or most preferably 150 to 200 deg C.

The ionophore may be any of the art, depending on the desired application, including tetra(p-chloro)phenylborate (TCPB) for cationic analytes, or methyltridodecylammoniumchloride (MTDDACl) for anionic analytes or any of those listed in FIG. 11.

The composition of the membrane components (base+curing agent+ionophore) in step (c3), may comprise less than 0.1, 0.25, 0.5, 0.75, 1, 1.5, 2, 2.5, 3, 4, 5, 6, 7, 8, 9 or 10% ionophore or a value in the range between any of the two aforementioned percentages, preferably 0.1 to 3%, more preferably 0.5 to 2.5% and most preferably 1 to 2% ionophore.

Ion pairs can be introduced as described above or can be introduced by swelling in organic solvents containing the analyte. The preferred solvents are THF or DOS.

Properties of the polysiloxane can be tuned by introduction of DOS or other plasticisers. Silicon used was Sylgard 184 DOW CORNING.

In the construction of gradient polymer comprising two 'back to back' gradients described previously, any two of the above mentioned gradient polymers or electrodes are joined together at the surface of the membrane region (or lowest concentration of electrically conducing particles) by means of the solvent (e.g. THF, DMSO).

FIG. 1 depicts a cross-section of an example of a potentiometric electrode 9, according to the invention. The electrode comprises a housing (isolator) 5, polymeric material 10, 11 and an electrical connection 2. Electrically conducting particles 3, are disposed in the conducing composite 10. Ionophores 4 are disposed in the membrane region 11. The ionophores 4 are least concentrated towards the electrical connection 10 exit end of the cylinder, and most concentrated towards the sample contact end 8 of the cylinder. The ionophores 4 and the electrically conducting particles 3 mix in a transition region 12.

FIG. 2 depicts a cross-section of another example of a potentiometric electrode 9, according to the invention. The electrode comprises a housing (isolator) 5, cylinder made from polymeric material 1 and an electrical connection 2. Electrically conducting particles 3, are disposed in a gradient 6 through the polymeric material 1. The electrically conducting particles 3 are most concentrated towards the electrical connection 2 exit end of the polymeric material 1, and least concentrated towards the sample contact end 8 of the polymeric material. Ionophores 4 are disposed in a gradient 7 through the polymeric material. The ionophores 4 are least concentrated towards the electrical connection-exit end of the cylinder 1, and most concentrated towards the sample contact end 8 of the polymeric material. The ionophores 4 and the electrically conducting particles 3 mix in a transition region.

FIGS. 10A and 10B depict an example of a flow cell 17 according to the invention. The outlet of an HPLC column 18 connects to an inlet 19 to the flow cell 17. One or more spraying devices 15 provide a spray of eluent 16, which is directed over the sample contact surface 8 of the electrode 9 of the present invention. A reference electrode 13 is also present in the flow cell. FIG. 10B illustrates the simple removal and insertion of the electrode 9 from the flow cell 17.

EXAMPLES

The invention is illustrated by means of the following non-limiting examples

1a. Preparing an Electrode (A).

A composite material forming the substantial part of the electrode was made by preparing a suspension of graphite particles and PVC in THF (tetrahydrofuran). The composite material was provided onto a copper electrode by evaporating the suspension thereon. After drying the composite material, the electrode was extended by the addition of ionophore-containing layers as follows.

Several mixtures were prepared, each containing a different ionophore.

A mixture containing compounds 1 to 4 as ionophore comprised 1% compound, 0.2% methyltridodecylammonium chloride (MTDDACl), 33% PVC and 65.8% plasticiser as the final layer contacting the sample.

The mixtures based on compounds 5-8 and 10 comprised 1% ionophore, 33% PVC, and 66% plasticiser as the final layer contacting the sample.

A mixture incorporating compound 9 comprised 1% ionophore, 27% PVC and 72% plasticiser as the final layer contacting the a sample.

A mixture based on MTDDACl as an ionophore contained 6% MTDDACl, 33% PVC and 61% plasticiser as the final layer contacting the sample.

The anion-sensitive electrodes were conditioned with the running eluent in the LC system until a stable baseline was obtained (few hours).

1b. Preparing an Electrode (Alternative B).

An electrode suitable for use in HPLC potentiometric sensing is made of a PVC cylinder (1×5 cm) with a central hole of 3 mm diameter (see, for example, FIG. 1). One side of the hole is sealed by a copper rod. The other side of the hole is filled with conducting composite of 60% graphite and 40% PVC:

1) A suspension of 60% graphite and 40% high molecular weight PVC in THF (1/3 ratio/solid THF) is prepared by mixing and stirring.

2) The hole is filled with the suspension of step (1).

3) The suspension is dried by room or elevated temperature.

4) Step 2 and 3 are repeated until the hole is completely filled.

5) The surplus of graphite/PVC composite is removed by grinding and polishing.

The membrane and the gradient are prepared as described:

1) 65% DOS, 32% PVC and 2% TCPB are mixed in a 100 mg quantity.

2) This mixture is dissolved in 1 ml THF

3) One drop (25 ul) is deposed onto the cylinder.

4) THF is evaporated at room temperature (~5 mm).

5) Step 3 and 4 are repeated at least three times (in total).

Note: the gradient is formed by dissolving of the composite (60% graphite 40% PVC) in the membrane/THF solution. Using the described procedure one obtains a ±200 um layer in which the concentration of DOS and ions gradually decreases and the concentration of PVC and graphite gradually increases. After hydration one obtains a working electrode.

Life Span in HPLC Applications

The life span of two electrodes was tested by continuous exposure to a flow of distilled water at a flow rate of 1 ml/mm. At regular intervals the quality of the electrodes was tested by HPLC experiments. These consisted of the separation and potentiometric detection of 6 amines (methyl-, ethyl-, propyl-, butyl-, pentyl- and hexylamine) on a universal cation column (4.6×100 Alltech) with a 1 mM $HNO_3$ 5% Acetonitrile eluent. After 4 months and 127 liters of distilled water, the quality of the electrodes was still acceptable for routine potentiometric measurements. The studied time span is equivalent with 1 year of use with a workload of 40 hours/week at a 1 ml/mm flow rate.

1c. Preparing an Electrode (Alternative C)

The electrodes for HPLC applications may be adapted to the specific needs of the dissolution application.

The electrodes for use in dissolution applications are prepare as described in Example 1b. The PVC cylinder is glued onto a hollow glass tube with a diameter of 3 mm. In order to protect the glue from the samples, a silicon tube is positioned over the glass PVC transition.

In order to obtain reproducible measurements in batch (dissolution) the analyte is present as ion pair in the electrode membrane. In order to obtain this ion pair there are three possible procedures:

1) Introduction of the ion pair by adding it to the membrane components during fabrication (step 1 of membrane preparation).

2) Adding the analyte to the membrane mixture during step 1 or 2 of membrane preparation.

3) Post production formation of the ion pair: the ion pair is formed by direct contact of the electrode with a solution of the analyte (e.g. 30 mg/900 ml dapoxetune/0.1M HCl). During this process the analyte is extracted from the solution into the electrode, and the ion pair is formed in situ. This process takes typically up to 5 hours.

Life Span in Dissolution Applications

The experimental data enables us to deduce a live span of ~6 months for the electrodes in dissolution applications.

1d. Preparing an Electrode (Alternative D)

Alternative preparation of the composite. A uniform composite can be obtained by following method:

1) A suspension of 60% graphite and 40% high molecular weight PVC in THF (1/3 ratio solid/THF) is prepared by mixing and stirring.

2) The mixture is injected in distilled water and precipitates.

3) The precipitate is reduced in size by blending.

4) The precipitate is filtered and dried.

5) The dry residue is pressed into a pellet by a IR pellet press (3 ton).

6) The composite pellet is fixed in a PVC tube and a copper wire is inserted.

Membrane deposition and gradient formation are identical to the previous methods (Examples 1b, 1c).

1e. Preparing an Electrode (Alternative E)

In the poly(butylacrylate) membrane electrode, PVC and plasticiser can be replaced by poly(butylacrylate) in the construction of the electrodes. The replacement can be partial i.e. PVC and DOS are replaced by poly(butylacrylate) during membrane and gradient construction, or complete i.e. all PVC (except the isolator) is replaced by poly(butylacrylate).

In the first case the electrode construction is 60% graphite, 40% PVC/gradient/98% poly(butylacrylate), 2% ions and ionophores In the second case the electrode consists of 60% graphite, 40% poly(butylacrylate)/gradient/poly(butylacrylate), 2% ions and ionophores Poly(butylacrylate) composite can be used as base for non poly(butylacrylate) based membranes, e.g. PVC/DOS. In this case the composition of the electrode is: 60% graphite, 40% poly(butylacrylate)/gradient/65% DOS, 32% PVC, 2% ions and ionophores.

Note: The 60% graphite 40% poly(butylacrylate) composite is an ideal self gluing base for mounting of any polymer based membrane.

Poly(n-butylacrylate) can be replaced by cross linked poly (butylacrylate), cross linking is initiated after mixing all components and after creation of the gradient.

1f. Preparing an Electrode (Alternative F)

The polysiloxane membrane electrode is constructed as follows:

1) In a hollow glass tube a paste is introduced in which an electrical conductor (copper wire) is fitted as schematically depicted in FIG. 1.

This paste consists of:

60% graphite (1-2 micron) 30% PVC, or

60% graphite (1-2 micron) 30% polysiloxane, or

60% graphite (1-2 micron) 30% DC 200 silicon oil,

2) On this layer polysiloxane is applied as described:

Base and curing agent are mixed and ~2% TCPB and/or ionophore are added. In order to become a more extended gradient this mixture can be dissolved in THF. Typically a 2/1 ratio mixture/THF is applied.

The mixture (with our without THF) is applied onto the paste of step 1). The construction is degassed by vacuum. The electrode is heated to 150-200 deg C.; the temperature depends on the ratio base/curing agent. After hydration one obtains a working electrode.

Ion pairs can be introduced as described above (Example 1c) or can be introduced by swelling in organic solvents containing the analyte. The preferred solvents are THF or DOS.

Properties of the polysiloxane can be tuned by introduction of DOS or other plasticisers. Silicon used was Sylgard 184 DOW CORNING.

1g. Preparing an Electrode (Alternative G)

1) A suspension of 60% graphite and 40% high molecular weight PVC in THF (1/3 ratio solid/THF) is prepared by mixing and stirring.

2) The mixture is injected in distilled water and precipitates.

3) The precipitate is reduced in size by blending.

4) The precipitate is filtered and dried.

5) The dry residue is pressed into a pellet by a IR pellet press (3 ton).

6) The composite pellet is fixed in a PVC tube and a copper wire is inserted.

7) 65% DOS, 32% PVC and 2% TCPB are mixed in a 100 mg quantity.

8) This mixture is dissolved in 1 ml THF

9) One drop (25 ul) is deposed onto the cylinder.

10) THF is evaporated at room temperature (~5 nin).

11) Step 3 and 4 are repeated at least three times (in total).

12) Make a second component by repeating step 1-11

13) Glue both membrane sides of the gradient polymer together by means of solvent (THF).

2. Synthesis of the Compounds 1 to 10.

Compounds 1 and 2:

Tris(2-aminoethyl)amine was mixed with 3 equiv. of octadecyl isocyanate, or phenyl isocyanate in chloroform solution at room temperature. After vigorous exothermic reaction, the mixtures were heated at reflux for 3 hours, cooled to room temperature, filtered off, washed with chloroform and dried.

Yield of 1: 87%, 2—93%. LSIMS (NBA): 1—1032 $(M+H)^+$, 2—504 $(M+H)^+$

Compound 3:

2,6-Diaminopyridine was dissolved in warm cyclohexane to obtain a clear solution. To this hot solution one equivalent of octadecyl isocyanate was added slowly. The mono substituted product precipitated during the reaction course, preventing the product from double substitution. After cooling, the white product was filtered off, washed with cyclohexane and dried at reduced pressure.

Yield quantitative. LSIMS (NBA): 405 $(M+H)^+$

Compound 4:

2,6-Diaminopyridine was dissolved in warm chloroform to obtain a clear solution. To this hot solution, two equivalents of octadecyl isocyanate were added slowly. The disubstituted product precipitated during the reaction course. After cooling, a double amount of hexane was added to precipitate the compound. The white product was filtered off, washed with hexane and dried at reduced pressure.

Yield 95%. LSIMS (NBA): 700 $(M+H)^+$

Compound 5:

The hexaaza compound with secondary amino functions was synthesized as described in Pauwels, T. F.; Lippens, W.; Herman, G. G.; Goeminne, A. M. *Polyhedron* 1998, 17, 1715-23, and Menif, R.; Martell, A. E. *Journal of the Chemical Society-Chemical Communications* 1989, 1521-23. Its N-hexaoctyiderivative was obtained as follows: The solution of the hydrochloride salt of the hexa-aza compound (0.40 g, 0.62 mmol) and $K_2CO_3$ (5 g) in 200 ml dry acetonitrile was stirred for 24 h under nitrogen blanket. A solution of n-octyl-bromide (0.78 g, 4 mmol) in 50 ml of dry acetonitrile was added dropwise to the stirred mixture. A catalytic amount of tetrabutylammonium iodide (0.15 g) was added and the mixture was refluxed for two days. The warm mixture was filtered. The solvent was removed in vacuo to give a brownish oil to which 100 ml of sodium hydroxide solution (pH=12) and 100 ml of chloroform were added. The water phase was extracted several times with additional portions of 100 ml of chloroform. The chloroform layers were collected, dried over anhydrous $K_2CO_3$ and evaporated under reduced pressure. The resulting oil was purified by column chromatography on silica gel with chloroform-ethanol (80:20) as eluent, which gave a yellow oil after evaporating the eluent (201 mg, 30% yield).

1H-NMR (CDCl$_3$): δ 0.81 (t, 18H), 1.18-1.36 (m, 72H), 2.28-2.39 (m, 28H), 3.36 (s, 8H), 7.07-7.13 (m, 8H).

Compounds 6 and 7:

The synthesis of these compounds was described in Jarzebinska, A.; Pietraszkiewicz, M.; Bilewicz, R. *Materials Science & Engineering C-Biomimetic and Supramolecular Systems* 2001, 18, 61-64. Compounds 8, 9 and 10 were synthesized under an argon atmosphere.

Compound 8:

The starting hexaamine (structure as for compound 6 where R=R1=H, FIG. 11) was synthesized according to the procedure given by Pietraszkiewicz, M.; Gasiorowski, R. *Chemische Berichte* 1990, 123, 405-06. The solution of hexaamine (1 equiv.) and acrylonitrile (12 equiv.) was stirred for 6 h at 40° C. Evaporation yielded white solid. Then, the cyanide groups were reduced with LiAlH$_4$ (6 equiv.) in THF at reflux under Ar. After 5 hours, the excess of LiAlH$_4$ was quenched with 10% aqueous solution of NaOH. The isolated and dried compound was mixed with octadecyl isocyanate (6 equiv.) in dry THF at elevated temperature. The stirring was continued for 3 hours, then the solvent was evaporated. MeOH was added, and the formed solid was filtered off, washed with methanol, and dried in vacuum.

MALDI-TOF MS: 2547 (M$^+$).

Compound 9:

To the first generation of dendrimer based on a macrocyclic hexaamine (its synthesis was described in Pietraszkiewicz, M.; Gasiorowski, R. *Chemische Berichte* 1990, 123, 405-06), octadecyl isocyanate (12 equiv.) was added. The mixture was stirred continuously for 48 h at elevated temperature. The brown solid thus obtained was washed three times with warm EtOH. After cooling, the solid precipitated from the solvent. Next, the product was filtered and dried in vacuum.

MALDI-TOF MS: 5138.0 (M$^+$).

Compound 10:

To the rapidly stirred mixture of 4 g hexaamine (mentioned above) in THF at reflux, succinic anhydride (1 g) was added. Reflux and stirring was continued for 2 h. The succinic amido-acid derivative was filtered off, washed with cold THF and dried. The solid was reduced in this same way as described above for compound 8. After reduction, the solid was mixed with 30% aqueous formaldehyde (40 ml) and formic acid (30 ml) and heated for 6 h at reflux. Water and acid were evaporated and the product was dried in vacuum. In the next step the compound was dissolved in THF and stirred with octadecyl isocyanate (1 equiv.) for 6 h at elevated temperature. After evaporation of THF the solid was dried in vacuum.

MALDI-TOF MS: 904.6 (M$^+$); MS (ES$^+$): 904.7 (M$^+$)

4. Instrumentation

Liquid chromatography was performed using a Spectra Physics 8810 isocratic pump, a Valco injector (10 μL loop), column 125×4 mm filled with reversed-phase Lichrospher 100-5 RP-8, (Merck), eluent 1 mM $H_3PO_4$. The flow-rate was 0.5 mL min$^{-1}$. The column outlet was directed perpendicularly towards the sensitive membrane of the coated-wire electrode in a flow-cell (Zielinska, D.; Poels, I.; Pietraszkiewicz, M.; Radecki, J.; Geise, H. J.; Nagels, L. J. Journal of Chromatography A 2001, 915, 25-33). The distance from the LC tubing outlet to the electrode was 100 μm. The membrane potential was measured against an Orion 800500 Ross® reference electrode using a high impedance ($10^{13}$Ω) amplifier. The detection signals were recorded on a PC 1000 data acquisition system from Thermo Separation Products.

5. Potentiometric Detection of Organic Acids.

A set of 7 (mostly dicarboxylic) acids were used as test substances. These acids are widely found in nature, and in the food/beverage industry. These acids are quite hydrophilic, with log P values mostly lower than (−1) (see Table 1). Membranes, whose components display lipophilic character, have the tendency to be unsensitive to hydrophilic analytes. The choice of the ionophore host molecules is essential. Molecules forming the strongest complex with the ionophore are detected most sensitively.

FIG. 12: Upper tracing: Separation of the organic acids on a Lichrosphere 100-5 RP8 column (Merck), 125×4 mm, eluent 1 mM $H_3PO_4$ at 0.5 mL min$^{-1}$ flow-rate. 10 μL injection of a mixture of tartaric- (1, 1×10$^{-5}$M), malonic- (2, 2×10$^{-7}$M), malic- (3, 4×10$^{-6}$M), lactic- (4, 1×10$^{-4}$M), citric- (5, 1×10$^{-5}$M), fumaric- (6, 2×10$^{-5}$M), succinic acid (7, 2×10$^{-5}$M). Lower tracing: Same conditions as upper tracing, injection of commercial lager pills beer after filtration on a 0.45 μm filter. The electrode coating used contained 33.8% PVC, 66% o-NPOE, 0.2% MTDDACl, and 1% ligand 3.

All components were detected very sensitively, the highest sensitivity being obtained for malonic acid: peak nr. 2 is due to 120 pg. The detection limit for this acid is in the low picogram range. The lower tracing presents a chromatogram of an injected beer sample (lager pills, no cleanup except filtration over a 0.45 μm filter, no dilution, 10 μL injection) in the same conditions. Tartaric- (1) and lactic- (4) acid could be identified.

FIG. 13 shows a HPLC chromatogram recorded using a coated-wire electrode incorporating ligand 9 and TOTM. The compound 9, of dendrimeric type, is tightly packed with urea units. Injected concentration: 1×10$^{-5}$M, peak identification: (1) tartaric acid, (2) malonic acid, (3) malic acid, (4) lactic acid, (5) citric acid, (6) fumaric acid, (7) succinic acid. Electrodes based on compound 9 were less sensitive but showed preference for citric acid (peak 5 in the chromatogram of FIG. 13).

FIG. 14 shows chromatograms obtained using a coated-wire electrode incorporating ligand 10 and TOP as plasticiser. In case of the compound 10, there is only one carbamoyl group available. Trace A) Injected concentration: 1×10$^{-5}$ M, peak identification: (1) tartaric acid, (2) malonic acid, (3) malic acid, (4) citric acid, (5) fumaric acid, (6) succinic acid. Trace B) Injected concentration and peak identification: (1)

$5\times10^{-4}$ M tartaric acid, (2) $2\times10^{-4}$ M malonic acid, (3) $2\times10^{-4}$ M malic acid, (4) $5\times10^{-3}$ M lactic acid, (5) $5\times10^{-4}$ M citric acid, (6) $5\times10^{-6}$ M fumaric acid, (7) $5\times10^{-4}$ M succinic acid. Electrodes based on this compound are very sensitive for fumaric acid (FIG. 14).

Table 1 lists detection limits (in pmol injected) of the 7 organic acids, obtained with the chromatographic system described in Example 4, with different ionophores in the potentiometric detector.

TABLE 1 detection limits (in pmol injected) of electrodes for 7 organic acids.

| Acid | Log P | Minimum amount of acid (pmol) required for detection in electrodes comprising compound (cmpd) numbers below | | | | | | |
|---|---|---|---|---|---|---|---|---|
| | | Cmpd 1 | Cmpd 2 | Cmpd 3 | Cmpd 4 | Cmpd 5 | Cmpd 6 | MTDDACl |
| Tartaric | −1.39 | 20 | 12 | 11 | 23 | 55 | 20 | 200 |
| Malonic | −0.34 | 1.6 | 1.0 | 1.1 | 1.6 | 4 | 4 | 200 |
| Malic | −1.22 | 6.5 | 4.0 | 4.2 | 5.6 | 20 | 15 | 200 |
| Lactic | −1.31 | 830 | 910 | 650 | 1200 | 5000 | 1900 | 1000 |
| Citric | −1.65 | 23 | 10 | 7 | 15 | 10 | 50 | 200 |
| Fumaric | +0.49 | 280 | 140 | 60 | 310 | 650 | 80 | 300 |
| Succinic | −1.11 | 77 | 56 | 47 | 86 | 330 | 200 | 700 |

Comparing the data obtained for electrodes incorporating the quaternary salt MTDDACl, where only electrostatic interactions occur, it is clear that extra interactions originating from compounds, makes the membranes much more sensitive.

Thus for malonic acid detected on membranes modified by open chain urea (1-4) and macrocyclic compound 8 the detection limit is down to 1 pg (see Table 1). This is two orders of magnitude lower than for MTDDACl based electrodes. All other acids were also detected sensitively, at injected concentrations varying from $4\times10^{-4}$ to $2\times10^{-5}$ M.

With hexaamine ionophores possessing alkyl chains, (compounds 5 to 7, FIG. 11), detection limits are drastically reduced compared with MTDDACl-based electrodes for 4 of the 7 acids (tartaric, malonic, malic, citric), with the most drastic reduction for malonic acid. All the azamacrocycles with lipophilic alkyl chains display very similar selectivities and detection limits, regardless the size of the macrocyclic cavity (compounds 5 to 7).

Malonic acid, as monoanion, can interact with ionophores electrostatically and by hydrogen bonding (Menif, R.; Martell, A. E. *Journal of the Chemical Society-Chemical Communications* 1989, 1521-23). Moreover, this acid is less hydrophilic (except of fumaric acid) than other analytes.

The best results for compound 10 were observed for fumaric acid (see FIG. 14), but the level of detection of other acids was worse than that for MTDDACl. The compound 10 possesses only one large lipophilic tail with a functional group. Probably, the macrocyclic unit does not lie at the membrane-water interface. This could lead to diminished electrostatic interactions of the acids with the compound at the interface.

Generally, detection limits were in the order malonic- (best detected)<citric- malic- and tartaric-<fumaric- and succinic- <lactic acid. For the most sensitively detected acid, malonic acid, detection limits as low as 1 pmol (injected amount) are obtained. This is quite sensitive, but is still a factor of 100 above the detection limits obtainable with HPLC/potentiometric detection for basic drugs with high log P values (e.g. bromhexine, ambroxol and clenbuterol with log P values of 4.03, 3.24 and 2.91 respectively).

6. Calibration Curves

FIG. 15 shows calibration curves obtained for three acids, with an electrode comprising the octaazamacrocycle compound (compound 7). In batch techniques, potentiometric detectors are always used in that part of the calibration curve where the signal (mV) is linearly related to $\log(C_{analyte})$. The calibration curve from FIG. 15 shows a linear relationship between the signal (peak height or area) and the analyte concentration.

The correlation is high, i.e. p=0.99999 (n=5) for malonic acid and at least 0.97 (n=4) for all other acids listed in Table 1 (not all data are plotted in FIG. 15). When used in HPLC conditions, the classical methodology of potentiometry has to be somewhat adapted to the situation. With a potentiometric sensor which continuously monitors the signal, one can work in the lower part of the calibration curve. It has been shown theoretically (De Backer, B. L.; Nagels, L. J. *Analytical Chemistry* 1996, 68, 4441-45), that in this part of the calibration curve, a linear relationship should be expected between the injected concentration, and the peak area (or peak height). For all acids from Table 1, this linearity was obtained in the 1 to 100 µM region.

7. Long-Term Stability of the Electrodes

Electrodes containing the azamacrocyclic compounds 5 and 7 had an operational lifetime (continuous use in chromatographic conditions) of at least 3 months. Their calculated high log P values were 20.6 and 16.7, respectively. Electrodes containing azamacrocyclic compound 6 with a significantly lower logP of 9.18 had a reduced operational lifetime of a few weeks. The minimal lipophilicity log P, required for ionophore-containing electrodes with a lifetime of 30×24 (days)× (h) upon exposure to an aqueous solution is generally estimated to be around 10. Electrodes containing the open chain urea compounds 1 to 4 also had operational lifetimes in the order of 2 weeks. The log P values of compounds 1 to 4 are 25.4, 10.1, 9.6 and 18.6 respectively.

10 synthetic ligands were tested and compared as ionophores in electrode membranes which are responsive to carboxylic acids. All these ligands largely improved (in comparison to MTDDACl) detection limits for the HPLC determination of the di- and tricarboxylic acids. The highest sensitivities were obtained for the open-chain urea compound 3. Compound 7 combines high sensitivity with long operational lifetime.

8. Application in "Dissolution Testing" of Pharmaceutical Drugs.

Determining the rate of dissolution of an active pharmaceutical ingredient (API) from a dosage form is an important quality indicating test in the pharmaceutical industry. Potentiometric sensors can be very useful in this respect. Classical UV detection systems allow only a very limited concentration range to be measured as the useful linear dynamic range of a UV detector is limited (0-2 absorbance units). The output signal of a UV detector gets saturated because the detector's response is linearly related to the concentration of the dissolved substance. Potentiometric sensors have the advantage that their response is dependent on the logarithm of the concentration. This means that if one gets good signals at the low concentration side, even very high concentrations can be monitored without saturating the sensor output voltage. Such behaviour can be seen in FIG. 16. Moreover, potentiometric sensors do not suffer from factors limiting the use of spectroscopic methods such as effects of flow cell dimensions, turbidity, and the presence of undissolved particles and of air bubbles.

Dissolution of 8 mg galantamine (spherical particles in capsules marked "reminyl CR") in 100 ml 0.001 M HCl was monitored by a potentiometric electrode of the present invention. The HCl solution was stirred continuously with a magnetic stirring bar. In FIG. 17, curve B shows the output signal of the potentiometric sensor. The signal was monitored versus a reference electrode which was also hanging in the HCl solution. Curve A was calculated from curve B using the smoothed data from FIG. 16. It shows the concentration versus time behavior of the basic drug galantamine. The electrode used contained PVC, tetra(p-chloro)phenylborate (TCPB) as an ionophore, and DOS as a plasticiser.

The observed response profile gives a good description of the dissolution behaviour. The potentiometric electrode of the invention also allows measurements to be done in media which damage the coated wire type electrodes (e.g. media containing detergents).

What is claimed is:

1. A potentiometric electrode for selective analyte detection in a sample comprising:
a sensing body made from polymeric material comprising:
electrically conducting particles, which increase in concentration away from a sample contact surface,
ionophore molecules, which increase in concentration towards the sample contact surface, and
an electrical connection which passes proximal to said electrically conducting particles, wherein the ionophore molecules and the electrically conducting particles lack an interface and mix predominantly in a transition region, wherein the nearest boundary of the transition region is located between 1 and 400 micrometers from the sample contact surface.

2. The potentiometric electrode according to claim 1 wherein the polymeric material comprises one or more of poly(n-butylacrylate), poly(butylacrylate), cross-linked poly(butylacrylate), polycarbonate, polystyrene, polymethylmethacrylate, poly(vinylchloride-co-vinylacetate-co-vinylalcohol), polysiloxane, silicon oil, polyvinyl chloride, or high molecular weight polyvinyl chloride.

3. The potentiometric electrode according to claim 1 wherein said electrically conducting particles are selected from the group consisting of carbon powder, graphite powder, synthetic graphite powder and combinations thereof and wherein said conducting particles have a diameter of 1 to 2 micrometer.

4. The potentiometric electrode according to claim 1, wherein said electrically conducting particles are selected from the group consisting of electropolymerised materials, oxidized polypyrrole and its derivatives, oxidized polythiophenes, polyaniline, noble metals, gold, platinum and combinations thereof.

5. The potentiometric electrode according to claim 1, wherein said ionophore molecules are one or more selected from the group consisting of the compounds 1 to 10

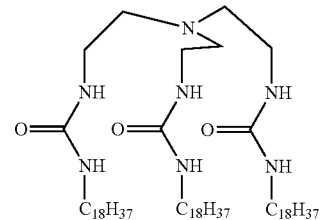

compound 1

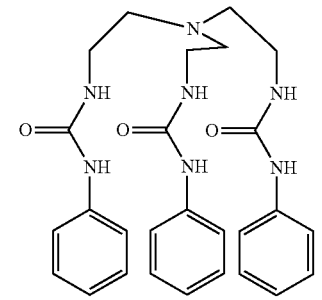

compound 2

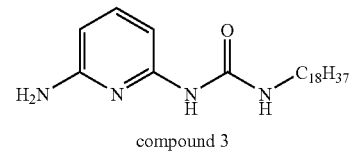

compound 3

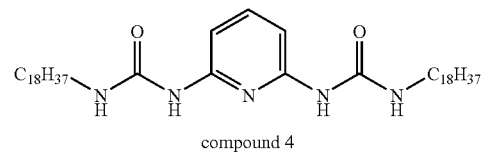

compound 4

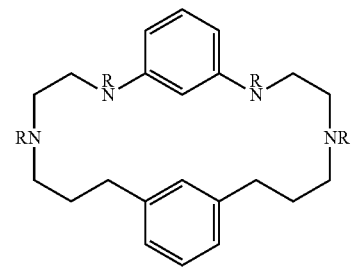

compound 5    $R = C_8H_{17}$

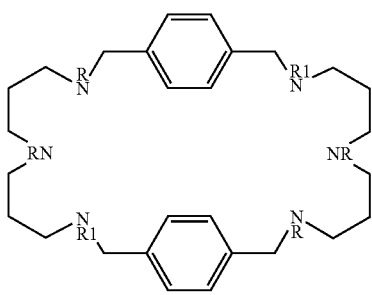

compound 6   R = H, R1 = C₁₀H₂₁
compound 8   R = R1 = (CH₂)₃NHCONHC₁₈H₃₇
compound 9   R =R1=CH₂CONHC₂H₄N(C₂H₄NHCONHC₁₈H₃₇)₂

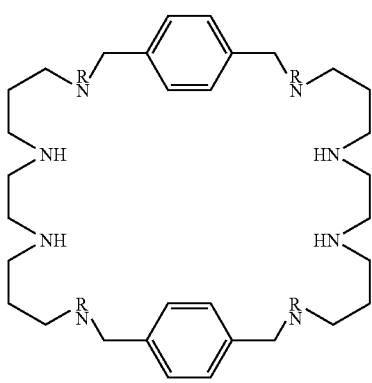

compound 7   R = C₁₀H₂₁

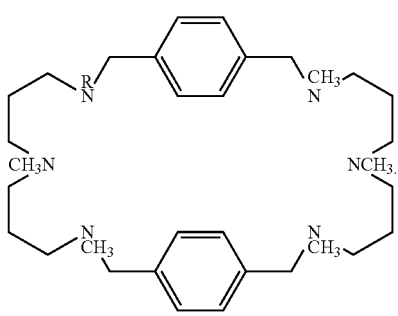

compound 10   R = (CH₂)₄OCONHC₁₈H₃₇

6. The potentiometric electrode according to claim 1 wherein said ionophore molecules are one or more selected from the group consisting of tetra (p-chloro)phenylborate, methyltridodecylammoniumchloride, compound 11: calix[6] arene, compound 12: calix[4]arene, compound 13: valinomycin, compound 14: nonactin, compound 15: amine ionofore 1, compound 16: dibenzo-18-crown-6, compound 17: Dibenzo-24-crown-8, compound 18: Dibenzo-30 crown-10, compound 19: cyclodextrin, compound 20: phosphoryl derivate, and the following compound:

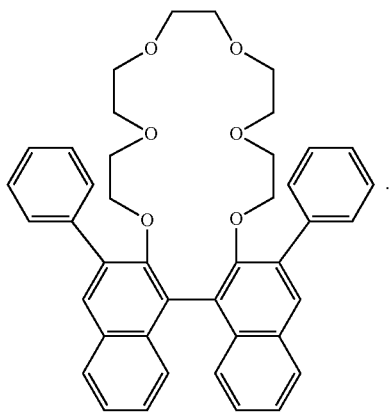

7. The potentiometric electrode according to claim 1 wherein the polymeric material is at least partly enclosed in a housing.

8. A potentiometric electrode according to claim 1 wherein the polymeric material comprises plasticiser and wherein the plasticiser is more disposed in a region of polymeric material comprising ionophore molecules, than the remainder of the polymeric material.

9. A method for making a potentiometric electrode according to claim 1 comprising the steps of:
(a) preparing a suspension of electrically conducting particles in a solution comprising polymeric material or polymer in a solvent,
(b) inserting an electrical conductor into the suspension,
(c) drying the suspension, so forming a solid composite polymer with electrically conducting particles therein,
(d) adding, to a surface of the composite of step (c) a solution comprising one or more of polymer, polymeric material, electrically conducting particles and ionophore molecules,
(e) drying the mixture,
(f) repeating steps (d) and (e), in such a manner, wherein the nearest boundary of the transition region is located between 1 and 400 micrometers from the sample contact surface, and
(g) obtaining a potentiometric electrode with composite gradient properties and no interfaces.

10. The method for making a potentiometric electrode according to claim 9, wherein the solution of step (a) comprises the polymer in a solvent, and wherein the solution of step (d) comprises polymer and ionophore,
whereby a potentiometric electrode is obtained.

11. The method for making a potentiometric electrode according to claim 9 wherein the solution of step (a) comprises the polymer in a solvent, and further comprising the steps of:
(b1) injecting the suspension into distilled water, so forming a precipitate,
(b2) reducing the size of the precipitate to form a residue,
(c1) drying the residue by pressing to form a conducting particle/polymer composite, followed by steps (d) to (g) as defined in claim 9.

12. The method according to claim 9 wherein the relative proportion (w/w) of said electrically conducting particles to said polymer is in the range 20 to 90% electrically conducting particles.

13. The method according to claim 9 wherein said electrically conducting particles are selected from the group consisting of carbon powder, graphite powder, synthetic graphite powder and combinations thereof and wherein said conducting particles have a diameter of 1 to 2 micrometer.

14. The method according to claim 9 wherein said electrically conducting particles are selected from the group consisting of polyaniline, noble metals, gold platinum, electropolymerised materials, oxidized polypyrrole and its derivatives, oxidized polythiophenes and combinations thereof.

15. The method according to claim 9 wherein said polymer is selected from the group consisting of poly(n-butylacrylate), poly(butylacrylate), polycarbonate, polystyrene, polymethylmethacrylate, poly(vinylchloride-co-vinylacetate-co-vinylalcohol), polysiloxane, silicone oil, high molecule weight polyvinyl chloride (PVC) and combinations thereof.

16. The method according to claim 9 wherein the proportion of the mass of solid components (electrically conducting particles and polymer), to the volume of solvent in the suspension of step (a) is 1:(1 to 10).

17. The method according to claim 9 wherein the solvent of step (a) is selected from the group consisting of DMSO, 1,1,1,-trichloro ethane, $CCl_4$, N,N-dimethylformamide and N,N-dimethylacetamide, THF and combinations thereof.

18. The method according to claim 9 wherein the solvent of step (d) is selected from the group consisting of DMSO, 1,1,1,-trichloro ethane, $CCl_4$, N,N-dimethylformamide and N,N-dimethylacetamide, THF and combinations thereof.

19. The method according to claim 9 wherein said ionophore molecules are one or more selected from the group consisting of compounds 1 to 10

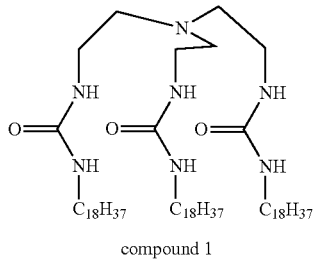

compound 1

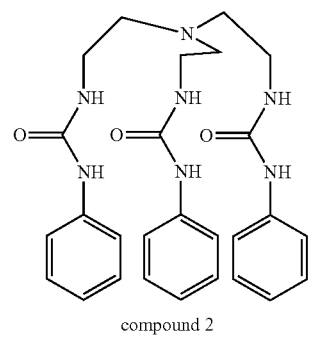

compound 2

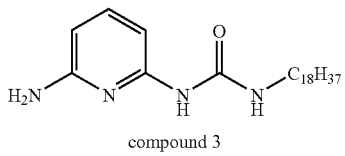

compound 3

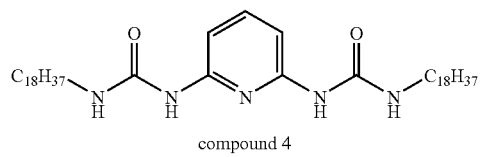

compound 4

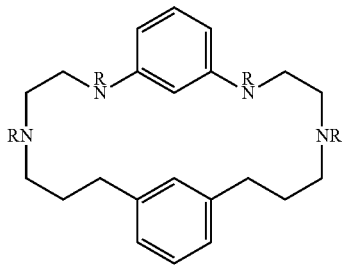

compound 5   R = $C_8H_{17}$

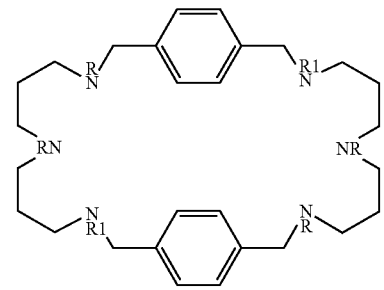

compound 6   R = H, R1 = $C_{10}H_{21}$
compound 8   R = R1 = $(CH_2)_3NHCONHC_{18}H_{37}$
compound 9   R = R1 = $CH_2CONHC_2H_4N(C_2H_4NHCONHC_{18}H_{37})_2$

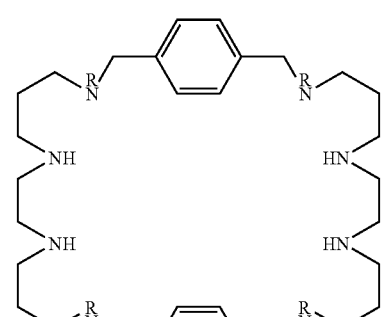

compound 7   R = $C_{10}H_{21}$

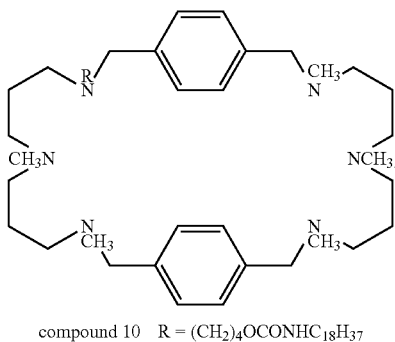

compound 10   R = (CH$_2$)$_4$OCONHC$_{18}$H$_{37}$

20. The method according to claim 9 wherein said ionophore molecules are one or more selected from the group consisting of tetra (p-chloro)phenylborate, methyltridodecylammoniumchloride, compound 11: calix[6]arene, compound 12: calix[4]arene, compound 13: valinomycin, compound 14: nonactin, compound 15: amine ionofore 1, compound 16: dibenzo-18-crown-6, compound 17: Dibenzo-24-crown-8, compound 18: Dibenzo-30 crown-10, compound 19: cyclodextrin, compound 20: phosphoryl derivate, and the following compound:

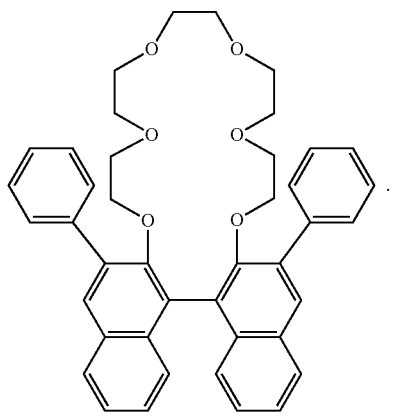

21. The method according to claim 9 wherein said polymer in step (d) is any which is in the rubber phase at or below room temperature.

22. The method according to claim 21 wherein said polymer in step (d) is poly(butylacrylate).

23. The method according to claim 21 wherein the composition of the solid components (polymer and ionophore) in step (d) comprises 85 to 99% polymer.

24. The method according to claim 21 wherein the composition of the solid components (polymer and ionophore) in step (d), comprises 0.1 to 3% ionophore.

25. The method according to claim 22 wherein the ratio (w/v) of solid components (polymer and ionophore) to solvent is 1:(8 to 12) in step (d).

26. The method according to claim 9 wherein the solution of step (d) further comprises plasticiser.

27. The method according to claim 26 wherein the composition of the membrane components (plasticiser, polymer and ionophore) in step (d) comprises 55 to 75% plasticiser.

28. The method according to claim 26 wherein said plasticiser is selected from the group consisting of o-nitrophenyl octyl ether, dioctyl sebacate, bis (2-ethylhexyl)phthalate, tris (2-ethylhexyl)phosphate, tris(2-ethylhexyl)trimellitate and combinations thereof.

29. The method according to claim 26 wherein the composition of the membrane components (plasticiser, polymer and ionophore) in step (d), comprise 28 to 38% polymer.

30. The method according to claim 26 wherein the composition of the membrane components (plasticiser, polymer and ionophore) in step (d), comprises 0.1 to 3% ionophore.

31. The method according to claim 26 wherein the ratio of the mass of membrane components (plasticiser, polymer and ionophore) to the volume of solvent is 1:(8 to 12) in step (d).

32. The method of claim 9, further comprising repeating steps (d) and (e) with decreasing concentrations of electrically conducting particles, and increasing concentrations of ionophore molecules.

33. A method for preparing a potentiometric electrode according to claim 1 comprising the steps of
   a3) preparing a paste comprising:
      a suspension of electrically conducting particles comprising polymeric material or a polymer, with or without solvent, or
      a suspension of electrically conducting particles comprising a polymer, with or without solvent, in which the polymer is polysiloxane, or
      a suspension of electrically conducting particles comprising a polymer, with or without solvent, in which the polymer is silicon oil,
   b3) inserting an electrical conductor therein,
   c3) adding to a surface of the particle/polymer composite a mixture comprising base, curing agent, and ionophore, optionally dissolved in solvent,
   d3) degassing the construction,
   e3) heating the construction, and
   f3) obtaining a potentiometric electrode with composite gradient properties and no interfaces.

* * * * *

UNITED STATES PATENT AND TRADEMARK OFFICE
CERTIFICATE OF CORRECTION

| | |
|---|---|
| PATENT NO. | : 7,857,962 B2 |
| APPLICATION NO. | : 11/587711 |
| DATED | : December 28, 2010 |
| INVENTOR(S) | : Nagels et al. |

It is certified that error appears in the above-identified patent and that said Letters Patent is hereby corrected as shown below:

First Page, Column 2, Abstract, Line 6, "same surface surface," should be changed to --same surface,--

Page 2, Column 1, Other Publications, Line 3, "Cycliczation of" should be changed to --Cyclization of--

Column 1, Line 55, "electrode contact," should be changed to --electrode contact.--

Column 4, Line 29, "111 trichloro ethane," should be changed to --1,1,1,-trichloro ethane,--

Column 4, Line 33, "111 trichloro ethane," should be changed to --1,1,1,-trichloro ethane,--

Column 4, Line 43, "to 21 in FIG. 11" should be changed to --to 21 in FIG. 11.--

Column 7, Line 4, "amine ionofore 1," should be changed to --amine ionophore 1,--

Column 10, Line 4, "concentration)" should be changed to --concentration).--

Column 11, Line 43, "towards the midpopint." should be changed to --towards the midpoint.--

Column 14, Line 31, "so called "walljet"." should be changed to --so called wall-jet".--

Column 15, Line 25, "obtained Ionphores may" should be changed to --obtained Ionophores may--

Column 16, Line 30, "mentioned above" should be changed to --mentioned above.--

Column 16, Line 37, "in daily use" should be changed to --in daily use.--

Column 17, Line 28, "111 trichloroethane," should be changed to --1,1,1,-trichloro ethane,--

Column 19, Line 47, "can very according" should be changed to --can vary according--

Column 20, Line 27, "184 (Dow Corning)" should be changed to --184 (Dow Corning).--

Column 22, Line 67, "dapoxetune (0.1M HCl)." should be changed to --dapoxetine (0.1M HCl).--

Signed and Sealed this
Twenty-fifth Day of October, 2011

David J. Kappos
*Director of the United States Patent and Trademark Office*

CERTIFICATE OF CORRECTION (continued)

Column 23, Line 35, "ionophores" should be changed to --ionophores.--

Column 23, Line 38, "ionophores" should be changed to --ionophores.--

Column 24, Line 33, "temperature (~5 nin)." should be changed to --temperature (~5 min).--

Column 30, Lines 54-64, " 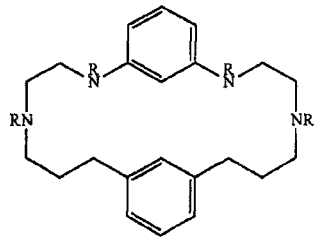 " should be changed to

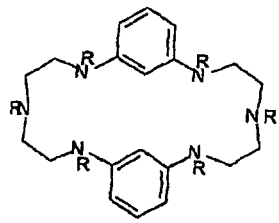

-- --

Column 31, Line 62, "amine ionofore 1," should be changed to --amine ionophore 1,--

Column 34, Lines 18-28, " 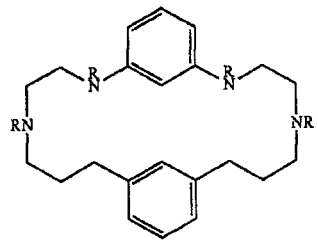 " should be changed to

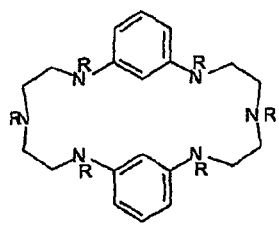

-- --

Column 35, Line 22, "amine ionofore 1," should be changed to --amine ionophore 1,--